US009546405B2

(12) United States Patent
Petrauskene et al.

(10) Patent No.: US 9,546,405 B2
(45) Date of Patent: *Jan. 17, 2017

(54) **DETECTION OF *LISTERIA* SPECIES IN FOOD AND ENVIRONMENTAL SAMPLES, METHODS AND COMPOSITIONS THEREOF**

(71) Applicant: LIFE TECHNOLOGIES CORPORATION, Carlsbad, CA (US)

(72) Inventors: Olga Petrauskene, San Carlos, CA (US); Craig Cummings, Pacifica, CA (US); Paolo Vatta, San Mateo, CA (US); Robert Tebbs, Austin, TX (US); Priya Balachandran, Foster City, CA (US); Patrick Zoder, Millbrae, CA (US); Lily Wong, San Mateo, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 121 days.

This patent is subject to a terminal disclaimer.

(21) Appl. No.: 14/309,865

(22) Filed: Jun. 19, 2014

(65) Prior Publication Data

US 2015/0045242 A1 Feb. 12, 2015

Related U.S. Application Data

(62) Division of application No. 13/174,622, filed on Jun. 30, 2011, now Pat. No. 8,795,969.

(60) Provisional application No. 61/360,273, filed on Jun. 30, 2010.

(51) Int. Cl.
*C12Q 1/68* (2006.01)
(52) U.S. Cl.
CPC ......... *C12Q 1/689* (2013.01); *C12Q 2600/156* (2013.01); *C12Q 2600/16* (2013.01)
(58) Field of Classification Search
CPC ............. C12Q 1/689; C12Q 2600/156; C12Q 2600/16
USPC ................................. 435/6.12, 91.2
See application file for complete search history.

(56) References Cited

U.S. PATENT DOCUMENTS

| 6,228,588 | B1 | 5/2001 | Benton et al. |
| 6,376,191 | B1* | 4/2002 | Yu ................ C12Q 1/6858 435/6.11 |
| 7,439,022 | B2 | 10/2008 | Hayashi |
| 8,795,969 | B2 | 8/2014 | Petrauskene et al. |
| 2002/0055116 | A1 | 5/2002 | Cunningham et al. |
| 2006/0078901 | A1 | 4/2006 | Buchrieser et al. |
| 2006/0286559 | A1 | 12/2006 | Hayashi |
| 2007/0161003 | A1 | 7/2007 | Morris et al. |

FOREIGN PATENT DOCUMENTS

| WO | WO02/28891 | 4/2002 |
| WO | WO2012/003409 | 5/2012 |

OTHER PUBLICATIONS

Bubert et al. "Detection and differentiation of *Listeria* spp. by a single reaction based on multiplex PCR", *Applied and Environmental Microbiology*, vol. 65, No. 10, Oct. 1, 1999, 4688-4692.
Intl Application No. PCT/US2011/042720, International Preliminary Report on Patentability mailed Jan. 8, 2013, 1-9.
Intl Application No. PCT/US2011/042720, International Search Report and Written Opinion mailed Dec. 14, 2011, 1-15.
Invitrogen, "MicroSEQ Listeria Monocytogenes Detection Kit", Detection Kit No. 4403874, 2009, 1.
Invitrogen, "TagMan Listeria Monocytogenes Detection Kit", Detection Kit 4366102, 2003-2004, 1-5.
Liu et al., "Gene Expression Profiling of Listeria Monocytogenes Strain F2365 During Growth in Ultrahigh-Temperature-Processed Skim Milk", *Applied and Environmental Microbiology*, vol. 74, No. 22, Nov. 2008, 6859-6866.
Lowe et al., "A computer program for selection of oligonucleotide primers for polymerase chain reactions", *Nucleic Acids Research*, vol. 18, No. 7, Apr. 11, 1990, 1757-1761.
McGann et al., "Temperature-Dependent Expression of Listeria Monocytogenes Internalin and Internalin-Like Genes Suggests Functional Diversity of These Proteins Among the Listeriae", *Applied and Environmental Microbiology*, vol. 73, No. 9, May 2007, 2806-2814.
Milohanic et al., "Transcriptome Analysis of Listeria Monocytogenes Identifies Three Groups of Genes Differently Regulated by PrfA", *Molecular Microbiology*, vol. 47, Issue 6 2003, 1613-1625.
The Nucleic Acid Sequence Search Report: AC : AEM74879, AUL95420, AR149315, G661131, Jun. 24, 2013, 1-2.
Rapose et al., "Listeria Grayi Bacteremia in a Heart Transplant Recipient", *Transplant Infectious Disease*, vol. 10, No. 6, Dec. 2008, 434-436.
Severino et al., "Comparative Transcriptome Analysis of Listeria Monocytogenes Strains of the Two Major Lineages Reveals Differences in Virulence, Cell Wall, and Stress Response", *Applied and Environmental Microbiology*, vol. 73, No. 19, Oct. 2007, 6078-6088.

(Continued)

*Primary Examiner* — Cynthia B Wilder
(74) *Attorney, Agent, or Firm* — Thompson Hine LLP

(57) ABSTRACT

Embodiments of the disclosure relate to isolated nucleic acid sequences, methods of use thereof, and workflows for detection of several *Listeria* species in a sample, particularly in a food or environmental sample. Embodiments of the disclosure may also be used to detect one or more species or strains of *Listeria* from each other, for example *L. grayi* may be detected independently of other *Listeria* spp. Some embodiments also describe a duplexed assay that can detect *L. monocytogenes, L. innocua, L. welshimeri, L. seelgeri, L. marthii* (formerly *incertae-sedis*), *L. ivanovii*, and *L. grayi*. Kits for detection of *Listeria* are also described. In some embodiments, methods and kits of the disclosure may comprise a TAQMAN® assay. In some embodiments, 0.2-2 cfu of *Listeria* spp. are detected using the compositions, methods and kits after a 24-28 hour enrichment period.

25 Claims, 11 Drawing Sheets

(56) References Cited

OTHER PUBLICATIONS

Shetron-Rama, et al., "Isolation of Listeria Monocytogenes Mutants With High-Level In Vitro Expression of Host Cytosol-Induced Gene Products", *Molecular Microbiology*, vol. 48, No. 6, 2003, 1537-1551.

Toledo-Arana, et al., "The Listeria Transcriptional Landscape from Saprophystism to Virulence", *Nature*, vol. 459, Jun. 18, 2009, 950-956.

\* cited by examiner

FIG. 1

SEQ ID NO: 1: CCTTGAAGGTGCCACAGTGACGAAGTTCCGGCAGAAATGCTCGGAAGTGGAACGAGGTAAACCCCACGAG CGAGAAACTCAAACTTATGGTAGGGGCACTTTTCCCGAGGAATCAAGA

Table 1:

| ASSAY ID | Target | FORSEQ | REVSEQ | PROBESEQ |
|---|---|---|---|---|
| 24728 | SEQ ID NO:1 | CGAAGTTCCGGCAGAAATGC<br>SEQ ID NO:2 | TGCCCCTACCATAAGTTTGAGTTTC<br>SEQ ID NO:3 | ACCTCGTTCCACTTCCG<br>SEQ ID NO:4 |
| 24729 | *rnpB of L grayi* | CCAAACTCTGACGGCAGGTAA<br>SEQ ID NO:5 | ACTTCGTCACTGTGGCACTTT<br>SEQ ID NO:6 | CAAGGCTACTACATCATATCT<br>SEQ ID NO:7 |
| 23800 | *rnpB of L. species* | AAAGCAGAGGAAAGTCCATGCT<br>SEQ ID NO:8 | GTTTGACCAGGCACGATCAC<br>SEQ ID NO:9 | TACGGGCATCACAGCAC<br>SEQ ID NO:10 |
| 23801 | SEQ ID NO:1 | CGGAAGTGGAACGAGGTAAACC<br>SEQ ID NO:11 | CTCGTCCCTTGTTCTTGATTCCT<br>SEQ ID NO:12 | ACCATAAGTTTGAGTTTCTC<br>SEQ ID NO:13 |
| 24107 | SEQ ID NO:1 | CCCACGAGCGAGAAACTCAA<br>SEQ ID NO:14 | CTCGTCCCTTGTTCTTGATTCCT<br>SEQ ID NO:15 | AAGTGCCCCTACCATAAGT<br>SEQ ID NO:16 |
| 24108 | SEQ ID NO:1 | CGAGCGAGAAACTCAAACTTATGGT<br>SEQ ID NO:17 | GCCTCGTCCCTTGTTCTTGATT<br>SEQ ID NO:18 | CCTCGGGAAAAGTG<br>SEQ ID NO:19 |
| 24109 | *rnpB of L. species* | GTGATGCCCGTAGTGATCG<br>SEQ ID NO:20 | AACGCTCTGTAAGCCATGTTC<br>SEQ ID NO:21 | n/a |
| ATCC19119.7s.1 | SEQ ID NO:1 | CGGAAGTGGAACGAGGTAAACC<br>SEQ ID NO:22 | GGAAAAGTGCCCCTACCATAAGTT<br>SEQ ID NO:23 | ACGAGCGAGAAACTCA<br>SEQ ID NO:24 |
| 16414292.7s.1 | SEQ ID NO:1 | GTGCCACAGTGACGAAGTTC<br>SEQ ID NO:25 | GCCCCTACCATAAGTTTGAGTTTCT<br>SEQ ID NO:26 | ACTTCCGAGCATTTCT<br>SEQ ID NO:27 |
| 16414292.8s.1 | SEQ ID NO:1 | AAATGCTCGGAAGTGGAACGA<br>SEQ ID NO:28 | AAGTGCCCCTACCATAAGTTTGAG<br>SEQ ID NO:29 | CCCCACGAGCGAGAAA<br>SEQ ID NO:30 |
| ATCC700545.1s.1 | *rnpB of L grayi* | CGTAGTGATCGTGCTTGGTGAAA<br>SEQ ID NO:31 | CCTGCCGTCAGAGTTTGGT<br>SEQ ID NO:32 | CTGCCTTGGCTTATTG<br>SEQ ID NO:33 |
| ATCC700545.2s.1 | *rnpB of L grayi* | GTGATCGTGCTTGGTGAAACAATAA<br>SEQ ID NO:34 | GGCACTTTCAAGGCTACTACATCAT<br>SEQ ID NO:35 | TACCTGCCGTCAGAGTTT<br>SEQ ID NO:36 |
| ATCC700545.3s.1 | *rnpB of L grayi* | ACGGCAGGTAAACCATCTAAGTC<br>SEQ ID NO:37 | CTTCGTCACTGTGGCACTTTC<br>SEQ ID NO:38 | AAGGCTACTACATCATATCTTAC<br>SEQ ID NO:39 |
| ATCC700545.4s.1 | *rnpB of L grayi* | GGCAGGTAAACCATCTAAGTCGTAA<br>SEQ ID NO:40 | GCGTTCCACTTCTGACATTTCTATC<br>SEQ ID NO:41 | TCACTGTGGCACTTTC<br>SEQ ID NO:42 |
| ATCC700545.5s.1 | *rnpB of L grayi* | GCCACAGTGACGAAGTTCTGAT<br>SEQ ID NO:43 | GCCCCTACCATAGTTTGAGTTTCTC<br>SEQ ID NO:44 | TCCACTTCTGACATTTCT<br>SEQ ID NO:45 |
| ATCC700545.7s.1 | *rnpB of L grayi* | CCCACGAGCGAGAAACTCA<br>SEQ ID NO:46 | CACCTCTTCCCTTGTTCAATTTCCT<br>SEQ ID NO:47 | AAGTGCCCCTACCATAGTT<br>SEQ ID NO:48 |

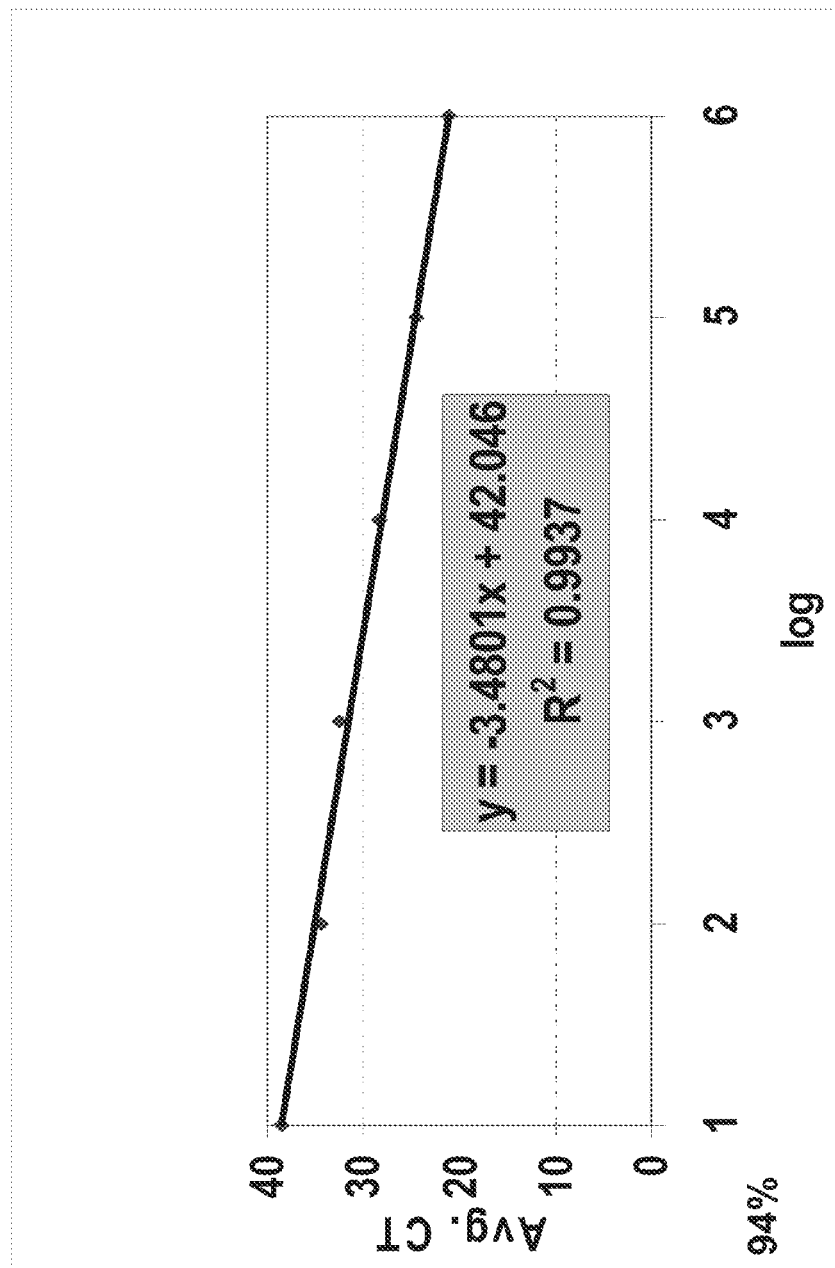
FIG. 3B Assay Efficiency: *L monocytogenes*

Table 11: Methods comparison for detection of Listeria species spiked into food and environmental surfaces

| Inoculation Level | Inoculating Organism | APC Count (Prior to Spike) | MPN/ 25 g & Inoculum Level-Env. Surfaces | Total Samples | Total + Samples (MicroSEQ and ISO) | MicroSEQ Listeria Species Method | | | | | ISO 11290-1 | $X^2$ (PrepSEQ vs. ISO 11290-1) | $X^2$ (Rapid Spin vs. ISO 11290-1) | Sensitivity Rate | | False Negative Rate | | False Positive Rate | |
|---|---|---|---|---|---|---|---|---|---|---|---|---|---|---|---|---|---|---|---|
| | | | | | | Automated PrepSEQ NA Presumptive | Automated PrepSEQ NA Confirmed | Rapid Spin Presumptive | Rapid Spin Confirmed | | | | | Automated PrepSEQ NA | Rapid Spin | Automated PrepSEQ NA | Rapid Spin | Automated PrepSEQ NA | Rapid Spin |
| *Hot Dogs* | | | | | | | | | | | | | | | | | | | |
| Control | N/A | | <0.075 | 5 | 0 | 0 | 0 | 0 | 0 | 0 | - | - | - | - | 0.0 | 0.0 | 0.0 | 0.0 |
| 0.2-2 CFU/ 25 g | *Listeria ivanovii* ATCC# 19119 | 6.0 x 10¹ | 0.52 | 20 | 9 | 8 | 8 | 8 | 8 | 2 | 4.68 | 4.68 | 400 | 400 | 0.0 | 0.0 | 0.0 | 0.0 |
| 2-5 CFU/ 25 g | *Listeria ivanovii* ATCC# 19119 | | 0.90 | 20 | 19 | 19 | 19 | 19 | 19 | 11 | 8.32 | 8.32 | 173 | 173 | 0.0 | 0.0 | 0.0 | 0.0 |
| *Roast Beef* | | | | | | | | | | | | | | | | | | | |
| Control | N/A | | <0.075 | 5 | 0 | 0 | 0 | 0 | 0 | 0 | - | - | - | - | 0.0 | 0.0 | 0.0 | 0.0 |
| 0.2-2 CFU/ 25 g | *Listeria innocua* NCTC 10528 | 4.6 x 10⁵ | 0.03 | 20 | 1 | 0 | 1 | 1 | 1 | 0 | 0.0 | 1.00 | 0 | 100 | 100 | 0.0 | 0.0 | 0.0 |
| 2-5 CFU/ 25 g | *Listeria innocua* NCTC 10528 | | 0.72 | 20 | 10 | 8 | 8 | 8 | 8 | 9 | 0.10 | 0.10 | 89 | 89 | 0.0 | 0.0 | 0.0 | 0.0 |
| *Lox* | | | | | | | | | | | | | | | | | | | |
| Control | N/A | | <0.075 | 5 | 0 | 0 | 0 | 0 | 0 | 0 | - | - | - | - | 0.0 | 0.0 | 0.0 | 0.0 |
| 0.2-2 CFU/ 25 g | *Listeria monocytogenes* ATCC# 49594 | 1.0 x 10² | 0.58 | 20 | 16 | 13 | 13 | 13 | 13 | 12 | 0.10 | 0.10 | 108 | 108 | 0.0 | 0.0 | 0.0 | 0.0 |
| 2-5 CFU/ 25 g | *Listeria monocytogenes* ATCC# 49594 | | 11.5 | 20 | 18 | 16 | 16 | 16 | 16 | 18 | .76 | .76 | 89 | 89 | 0.0 | 0.0 | 0.0 | 0.0 |

FIG. 5A

| Inoculation Level | Inoculating Organism | APC Count (Prior to Spike) | MPN/ 25 g & Inoculum Level-Env. Surfaces | Total Samples | Total + Samples (MicroSEQ and ISO) | MicroSEQ *Listeria* Species Method | | | | | | $X^2$ (PrepSEQ vs. ISO 11290-1) | $X^2$ (Rapid Spin vs. ISO 11290-1) | Sensitivity Rate | | False Negative Rate | | False Positive Rate | |
|---|---|---|---|---|---|---|---|---|---|---|---|---|---|---|---|---|---|---|---|
| | | | | | | Automated PrepSEQ NA Presumptive | Automated PrepSEQ NA Confirmed | Automated PrepSEQ NA Presumptive | Automated PrepSEQ NA Confirmed | Rapid Spin Presumptive | Rapid Spin Confirmed | ISO 11290-1 | | Automated NA PrepSEQ | Rapid Spin | Automated NA PrepSEQ | Rapid Spin | Automated NA PrepSEQ | Rapid Spin |
| Pasteurized whole milk | | | | | | | | | | | | | | | | | | | |
| Control | N/A | <10 | <0.075 | 5 | 0 | 0 | 0 | 0 | 0 | 0 | 0 | 0 | - | - | - | - | - | - | 0.0 | 0.0 |
| 0.2-2 CFU/ 25 g | *Listeria welshimeri* ATCC# 35897 | <10 | 0.23 | 20 | 7 | 4 | 4 | 4 | 4 | 4 | 4 | 5 | 0.14 | 0.14 | 80 | 80 | 0.0 | 0.0 | 0.0 | 0.0 |
| 2-5 CFU/ 25 g | *Listeria welshimeri* ATCC# 35897 | <10 | 0.52 | 20 | 20 | 16 | 16 | 16 | 16 | 16 | 16 | 14 | 0.52 | 0.52 | 114 | 114 | 0.0 | 0.0 | 0.0 | 0.0 |
| Dry Infant Formula | | | | | | | | | | | | | | | | | | | | |
| Control | N/A | 1.4 x 10³ | <0.075 | 5 | 0 | 0 | 0 | 0 | 0 | 0 | 0 | 0 | - | - | - | - | - | - | 0.0 | 0.0 |
| 0.2-2 CFU/ 25 g | *Listeria seeligeri* ATCC# 35967 | 1.4 x 10³ | 1.08 | 20 | 17 | 17 | 17 | 17 | 17 | 17 | 17 | 14 | 1.26 | 1.26 | 121 | 121 | 100 | 0.0 | 0.0 | 0.0 |
| 2-5 CFU/ 25 g | *Listeria seeligeri* ATCC# 35967 | 1.4 x 10³ | 2.32 | 20 | 20 | 20 | 20 | 20 | 20 | 20 | 20 | 19 | 1.00 | 1.00 | 105 | 105 | 0.0 | 0.0 | 0.0 | 0.0 |
| Stainless Steel | | | | | | | | | | | | | | | | | | | | |
| Control | N/A | N/A | 0.0 | 5 | 0 | 0 | 0 | 0 | 0 | 0 | 0 | 0 | - | - | - | - | - | - | 0.0 | 0.0 |
| 0.2-2 CFU/ 100 cm² | *Listeria welshimeri* ATCC# 43551 | N/A | <10 (100 *E. faecium*) | 20 | 10 | 7 | 7 | 7 | 7 | 7 | 7 | 9 | 0.41 | 0.41 | 78 | 78 | 0.0 | 0.0 | 0.0 | 0.0 |
| 2-5 CFU/ 100 cm² | *Listeria welshimeri* ATCC# 43551 | N/A | 60 (1,000 *E. faecium*) | 20 | | | | | | | | | | | | | | | 0.0 | 0.0 |

FIG. 5B

| Inoculation Level | Inoculating Organism | MPN/ 25 g & Inoculum Level- Env. Surfaces | Total Samples | Total + Samples (MicroSEQ and ISO) | MicroSEQ Listeria Species Method | | | | | ISO 11290-1 | $X^2$ (PrepSEQ vs. ISO 11290-1) | $X^2$ (Rapid Spin vs. ISO 11290-1) | Sensitivity Rate | | False Negative Rate | | False Positive Rate | |
|---|---|---|---|---|---|---|---|---|---|---|---|---|---|---|---|---|---|---|
| | | | | | Automated PrepSEQ NA Presumptive | Automated PrepSEQ NA Confirmed | Rapid Spin Presumptive | Rapid Spin Confirmed | | | | | Automated PrepSEQ NA | Rapid Spin | Automated PrepSEQ NA | Rapid Spin | Automated PrepSEQ NA | Rapid Spin |
| Plastic | | | | | | | | | | | | | | | | | | |
| Control | N/A | 0.0 | 5 | 0 | 0 | 0 | 0 | 0 | 0 | - | - | - | - | 0.0 | 0.0 | 0.0 | 0.0 |
| 0.2-2 CFU/ 100 cm² | Listeria seeligeri ATCC# 51335 | 0.8 | 20 | 2 | 2 | 2 | 2 | 2 | 0 | 2.05 | 2.05 | NA | NA | 0.0 | 0.0 | 0.0 | 0.0 |
| 2-5 CFU/ 100 cm² | Listeria seeligeri ATCC# 51335 | 18 | 20 | 15 | 9 | 9 | 9 | 9 | 7 | 0.41 | 0.41 | 128 | 128 | 0.0 | 0.0 | 0.0 | 0.0 |
| Ceramic Tile | | | | | | | | | | | | | | | | | | |
| Control | N/A | 0.0 | 5 | 0 | 0 | 0 | 0 | 0 | 0 | - | - | - | - | 0.0 | 0.0 | 0.0 | 0.0 |
| 0.2-2 CFU/ 100 cm² | Listeria grayi ATCC# 19120 | < 10 | 20 | 1 | 0 | 0 | 0 | 0 | 1 | 1.00 | 1.00 | NA | NA | 0.0 | 0.0 | 0.0 | 0.0 |
| 2-5 CFU/ 100 cm² | Listeria grayi ATCC# 19120 | 100 | 20 | 9 | 6 | 6 | 6 | 6 | 4 | 0.52 | 0.52 | 150 | 150 | 0.0 | 0.0 | 0.0 | 0.0 |
| Rubber | | | | | | | | | | | | | | | | | | |
| Control | N/A | 0.0 | 5 | 0 | 0 | 0 | 0 | 0 | 0 | - | - | - | - | 0.0 | 0.0 | 0.0 | 0.0 |
| 0.2-2 CFU/ 5 cm² | Listeria innocua NCTC# 11228 | 1.8 | 20 | 14 | 10 | 10 | 10 | 10 | 7 | 0.90 | 0.90 | 143 | 143 | 0.0 | 0.0 | 0.0 | 0.0 |
| 2-5 CFU/ 5 cm² | Listeria innocua NCTC# 11228 | 18 | 20 | 19 | 19 | 19 | 19 | 19 | 18 | 0.35 | 0.35 | 106 | 106 | 0.0 | 0.0 | 0.0 | 0.0 |

FIG. 5C

| Inoculation Level | Inoculating Organism | MPN/ 25 g & Inoculum Level- Env. Surfaces | Total Samples | Total + Samples (MicroSEQ and ISO) | MicroSEQ Listeria Species Method | | | | | ISO 11290-1 | X² (PrepSEQ vs. ISO 11290-1) | X² (Rapid Spin vs. ISO 11290-1) | Sensitivity Rate | | False Negative Rate | | False Positive Rate | |
|---|---|---|---|---|---|---|---|---|---|---|---|---|---|---|---|---|---|---|
| | | | | | Automated PrepSEQ NA Presumptive Confirmed | Automated PrepSEQ NA Confirmed | Rapid Spin Presumptive | Rapid Spin Confirmed | | | | | Automated NA PrepSEQ | Rapid Spin | Automated NA PrepSEQ | Rapid Spin | Automated NA PrepSEQ | Rapid Spin |
| Sealed Concrete | | | | | | | | | | | | | | | | | | |
| Control | N/A | 0.0 | 5 | 0 | 0 | 0 | 0 | 0 | 0 | - | - | - | - | - | - | - | 0.0 | 0.0 |
| 0.2-2 CFU/ 5 cm² | Listeria monocytogenes FSL-J1-049 | 2.0 | 20 | 4 | 3 | 3 | 3 | 3 | 1 | 1.08 | 1.08 | 300 | 300 | 0.0 | 0.0 | 0.0 | 0.0 |
| 2-5 CFU/ 5 cm² | Listeria monocytogenes FSL-J1-049 | 20 | 20 | 11 | 9 | 9 | 9 | 9 | 8 | 0.10 | 0.10 | 112 | 112 | 0.0 | 0.0 | 0.0 | 0.0 |

FIG. 5D

DETECTION OF *LISTERIA* SPECIES IN FOOD AND ENVIRONMENTAL SAMPLES, METHODS AND COMPOSITIONS THEREOF

CROSS REFERENCE TO RELATED APPLICATIONS

This patent application is division of U.S. application Ser. No. 13/174,622 filed Jun. 30, 2011, which claims priority under 35 U.S.C. §119(e) to U.S. Provisional Application No. 61/360,273 filed Jun. 30, 2010, the entire contents of which are incorporated herein by reference.

EFS INCORPORATION PARAGRAPH RELATING TO SEQUENCE LISTING

The instant application contains a Sequence Listing which has been submitted in ASCII format via EFS-Web and is hereby incorporated by reference in its entirety. Said ASCII copy, created on Jun. 24, 2011, is named LT0263US.txt and is 11,259 bytes in size.

FIELD OF DISCLOSURE

The present teachings relate to compositions, methods and kits for detection and identification of *Listeria* spp. More particularly, the specification describes compositions and kits comprising nucleic acid sequences specific and/or unique to *Listeria* spp. and methods of use thereof. Methods for differentially detecting *Listeria* spp. from other pathogens (*E. coli, S. aureus* and several others and various *Listeria* species and strains from each other (such as, but not limited to, *Listeria grayii* from several other *Listeria* spp.) are also described.

BACKGROUND

The detection of *Listeria* spp. is of particular interest for the food industry and for environmental monitoring. As an example of one of the most dramatic possibilities is contamination by the *Listeria monocytogenes* species which can lead to death in up to 25% of affected individuals. This has been the outcome of numerous outbreaks due to *L. monocytogenes* contaminated meat both in the United States and abroad. Even as this application is being written, the following news announcements appeared: "Georgia's Department of Agriculture has alerted consumers of the recall of cooked, fresh and frozen lobster meat by distributor Portland Shellfish Co. Inc. due to *listeria* bacteria contamination," and "Canadian Food Inspection Agency and Winnipeg-based Smith's Quality Meats are warning the public not to serve or consume all of the company's ready-to-eat cooked meats because they may be contaminated with *Listeria.*"

Up to 10% of humans may be intestinal carriers of *L. monocytogenes* and the bacteria have been found in domestic as well as feral mammalian species, as well as species of birds, fish and shellfish. The bacteria can be isolated from soil, silage, and other environmental sources. *L. monocytogenes* is quite hardy and resists the deleterious effects of freezing, drying, and heat remarkably well for a bacterium that does not form spores. Most *L. monocytogenes* are pathogenic to some degree. The organism has an unusual property of being able to cross the intestinal barrier, the blood-brain barrier and the placental barrier.

*L. ivanovii* has been considered to infect ruminants only. However, Guillet et al. report human listeriosis caused by *L. ivanovii* in the January, 2010, issue of *Emerging Infectious Diseases*. The isolate was indistinguishable from prototypic ruminant strains and thus, the organism is described as an enteric opportunistic human pathogen. Occasional human infections due to *L. seeligeri* have also been reported.

In general, *L. innocua, L. welshimeri, L. seeligeri, L. marthii* and *L. grayi* are considered nonpathogenic species. However, a case of *L. grayi* bacteremia in a patient with advanced Hodgkin's disease was reported in the *European Journal of Clinical Microbiology & Infectious Disease* (1998) and in a heart transplant recipient in 2008 (Transplant Infectious Disease, Vol. 10, Rapose et al.). All *Listeria* species are potential food contaminants; the presence on food of any of these species can be considered to be an indicator of contamination and of the potential presence of *L. monocytogenes*. Traditional culture confirmation methods used in food and environmental safety testing are lengthy and time-to-result can be greatly reduced by using rapid molecular methods.

U.S. Published Patent Application No. 2006/0078901 to the Pasteur Institute reportedly provides the genome sequence and nucleotide sequences of *L. monocytogenes* EGD-e. U.S. Pat. No. 7,439,022 relates to nucleic acids for detection of *Listeria* and reports alignments of sequences from five *Listeria* species for each of rnpB and rfn genes along with consensus sequences for each. Leclercq et al. (International Journal of Systematic and Evolutionary Microbiology, Nov. 13, 2009) reported a *Listeria*-like strain isolated from pre-cut lettuce that was differentiated from other species of *Listeria* by using phenotypic tests. They proposed the species name *Listeria rocourtiae* for the new species. The type strain is said to be avirulent as assessed by cell culture assays and inoculation of mice.

Early detection of the presence of *Listeria* is extremely important both from a public health perspective and from an economic perspective.

SUMMARY OF DISCLOSURE

In some embodiments, the disclosure describes isolated nucleic acid sequences for highly specific amplification and detection of *Listeria* species. In some embodiments, isolated nucleic acid sequences of the disclosure provide the ability to distinguish *L. grayi* from other *Listeria* species.

In some embodiments, a nucleic acid sequence of the disclosure may be described as a "target" sequence or a "target *Listeria* spp. nucleic acid sequence" and may comprise isolated nucleic acid molecules coding for a *Listeria* rnpB gene or a fragment thereof that is found in one or more *Listeria* spp. and generally absent in other non-*Listeria* organisms.

In some embodiments, a target nucleic acid sequence of the disclosure may comprise a nucleotide sequence of SEQ ID NO: 1, a fragment thereof, and/or a complement thereof. In some embodiments, a target *Listeria* spp. nucleic acid sequences may comprise isolated nucleic acid molecules comprising a nucleotide sequence having at least a 90% sequence identity, at least 80% sequence identity and/or at least 70% sequence identity to the nucleotide sequences of SEQ ID NO:1, a fragment thereof and/or a complement thereof.

The target nucleic acid sequence of SEQ ID NO: 1, represents a conserved rnpB gene found in most *Listeria* spp. SEQ ID NO: 1 is conserved in several *Listeria* spp. including *L. monocytogenes, L. innocua, L. ivanovii, L. welshimerii, L. marthii* and *L. seeligeri*. The disclosure may also describe additional target nucleic acid sequences specific for one or more other *Listeria* species and/or strains.

In some embodiments, the disclosure describes isolated nucleic acid sequence compositions that are designed as primers and probes. In some embodiments probe and primers of the disclosure are described in the nucleic acid sequences in SEQ ID NO: 2-SEQ ID NO: 48, and in nucleic acid molecules with at least 90% sequence homology to nucleic acid sequences of SEQ ID NO:2-SEQ ID NO:48, and in any nucleic acid molecule complementary to at least one sequence of SEQ ID NO:2-SEQ ID NO:48.

Accordingly, in some embodiments, the disclosure describes compositions comprising at least one isolated nucleic acid molecule having the nucleic acid sequence of: a) SEQ ID NO:2-SEQ ID NO:48, b) a nucleic acid molecule with at least 90% sequence homology to SEQ ID NO:2-SEQ ID NO:48, or c) a nucleic acid molecule complementary to at least one sequence of a) or b).

In some embodiments, isolated nucleic acid sequence compositions of the disclosure may further comprise one or more label, such as, but not limited to, a dye, a radioactive isotope, a chemiluminescent label, a fluorescent moiety, a bioluminescent label an enzyme, and combinations thereof, and may be referred to as a labeled derivative.

In certain embodiments, a composition of the disclosure may comprises isolated nucleic acid molecules having a primer pair combination and may comprise a primer pair (forward and reverse primer combination) comprising nucleic acid molecules described for example in any row of in Table 1 in FIG. 1. A composition of the disclosure may further comprise a probe described in the same row. A few example combinations of primer pairs (and probes) are described below, however, one of skill in the art, in light of this specification, will recognize that other combinations are also encompassed by the present disclosure.

For example, a composition of the disclosure may comprise a nucleic acid composition having SEQ ID NO:2 and SEQ ID NO:3, or nucleic acid molecules with at least 90% sequence homology thereto and may include labeled derivatives thereof. In further embodiments, the composition may further include an isolated nucleic acid molecule consisting of SEQ ID NO:4 or a nucleic acid molecule with at least 90% sequence homology thereto and may include labeled derivatives thereof.

In another example embodiment, a composition comprises isolated nucleic acid molecules consisting of SEQ ID NO:5 and SEQ ID NO:6, or nucleic acid molecules with at least 90% sequence homology thereto and may include labeled derivatives thereof. In further embodiments, this composition may further comprise an isolated nucleic acid molecule consisting of SEQ ID NO:7 or a nucleic acid molecule with at least 90% sequence homology thereto and may include labeled derivatives thereof.

The disclosure also describes recombinant constructs comprising nucleic acid sequences unique to *Listeria* spp and/or certain *Listeria* species and strains described in SEQ ID NO: 1-SEQ ID NO: 48 in sections above.

The present disclosure, in some embodiments, describes assay utilizing molecular methods such as sequence specific amplification and detection that offer significant improvements in speed, sensitivity and specificity over traditional microbiological methods. Embodiments relate to design and development of molecular detection assays comprising identification of target sequences that are present in *Listeria* spp and/or certain *Listeria* species and strains and absent or divergent in organisms not to be detected. Detection of one or more of such a target sequence or a fragment thereof in a sample is indicative of the presence of an organism of the *Listeria* spp and/or a certain *Listeria* species and/or a certain *Listeria* strain in that sample.

In some embodiments, methods of detecting the presence of *Listeria* spp and/or certain *Listeria* species and/or strains and/or serotypes in a sample are disclosed.

In some embodiments, a method of the disclosure, may comprise detecting, in a sample, at least one (or more) nucleic acid sequence(s) having at least 10 to at least 25 nucleic acids of SEQ ID NO:1 and/or complementary sequences thereof, wherein detection of at least one nucleic acid sequence indicates the presence of an *Listeria* organism in the sample. In some embodiments this method may comprise detecting a *Listeria* organism of the species *L. monocytogenes*, *L. innocua*, *L. ivanovii*, *L. welshimerii*, *L. marthii* and/or *L. seeligeri*. In some embodiments this method may comprise detecting a *Listeria* organism that is not *Listeria grayi*. Methods of detection may also comprise identification steps and may further comprise steps of sample preparation. Such embodiments are described in detail in sections below.

Detection may be performed by a variety of methods, such as but not limited to, by a nucleic acid amplification reaction. In some embodiments the amplification reaction maybe an end-point determination, the amplification reaction maybe quantitative. The quantification may be a real-time PCR method. In some embodiments, the real-time PCR may be a SYBR® Green Assay or a TaqMan® Assay. Detection, in some embodiments, be performed by hybridization using probes specific to target sequences. According to some embodiments, combinations of amplification and hybridization may be used for detection.

In some embodiments, a method for the detection of a *Listeria* spp. in a sample comprises: a) hybridizing a first pair of PCR primers comprising a forward primer and a reverse primer (e.g., selected for example from a row in Table 1 shown in FIG. 1) that are operable to bind to and amplify a rnpB gene or fragment thereof found only in *Listeria* spp and not in other organisms; b) amplifying the rnpB gene or fragment thereof found only in *Listeria* spp and not in other organisms to form an amplified target nucleic acid product; and d) detecting the amplified target polynucleotide sequence product; wherein the detection of the amplified target polynucleotide sequence product is indicative of the presence of *Listeria* spp. in the sample.

In one embodiments, a method for determining the presence of a *Listeria* species in a sample comprises: combining the sample with a culture medium for enriching *Listeria* species for a time to generate a sample enriched for said species; extracting nucleic acid from at least some of the enriched sample; contacting the extracted nucleic acid with at least one primer pair having hybridization specificity for amplifying a rnpB gene of *Listeria* species, or a fragment of the rnpB gene of *Listeria* species comprising a primer pair having SEQ ID NO:5 and SEQ ID NO:6, or SEQ ID NO:31 and SEQ ID NO:32, or SEQ ID NO:34 and SEQ ID NO:35, or SEQ ID NO: 37 and SEQ ID NO:38, or SEQ ID NO:40 and SEQ ID NO:41, or SEQ ID NO:43 and SEQ ID NO:44, or SEQ ID NO:46 and SEQ ID NO:47, or a nucleic acid molecule with at least 90% sequence homology to said SEQ ID sequences under conditions to generate amplified nucleic acid; and detecting at least some of the amplified nucleic acid, thereby determining the presence of *Listeria* species in the sample. In some embodiments, at least two of the above referenced primer pairs may be used.

In some embodiments, a primer pair having hybridization specificity for amplifying a rnpB gene of *Listeria* species, or for amplifying a fragment of the rnpB gene of *Listeria* species, amplifies SEQ ID NO:1 or a fragment thereof. In some embodiments, a primer pair having hybridization specificity for amplifying SEQ ID NO:1, or a fragment thereof, comprises isolated nucleic acid sequences having SEQ ID NO:2 and SEQ ID NO:3, or a nucleic acid molecule with at least 90% sequence homology to said SEQ ID sequences or a labeled derivative thereof. In further embodiments, the conditions to generate amplified nucleic acid further include an isolated nucleic acid molecule consisting of SEQ ID NO:4, or a nucleic acid molecule with at least 90% sequence homology to said SEQ ID sequence or a labeled derivative thereof.

In further method embodiments, a primer pair having hybridization specificity for amplifying a rnpB gene of *Listeria* species, or for amplifying a fragment of the rnpB gene of *Listeria* species, comprises isolated nucleic acid sequences consisting of SEQ ID NO:8 and SEQ ID NO:9, or SEQ ID NO:11 and SEQ ID NO:12, or SEQ ID NO:14 and SEQ ID NO:15, or SEQ ID NO:17 and SEQ ID NO:18, or SEQ ID NO:20 and SEQ ID NO:21, or SEQ ID NO:22 and SEQ ID NO:23, or SEQ ID NO:25 and SEQ ID NO:26, or SEQ ID NO:28 and SEQ ID NO:29, or a nucleic acid molecule with at least 90% sequence homology to said SEQ ID sequences or a labeled derivative thereof. In certain embodiments, the extracted nucleic acid is contacted with isolated nucleic acid molecules having SEQ ID NO:2, SEQ ID NO:3, SEQ ID NO:5, and SEQ ID NO:6, or a nucleic acid molecule with at least 90% sequence homology to said SEQ ID sequence or a labeled derivative thereof. In some embodiments, the contacting includes contacting with 5'-labeled isolated nucleic acids SEQ ID NO:4 and SEQ ID NO:7, or a nucleic acid molecule with at least 90% sequence homology to said SEQ ID sequence. In some embodiments, the detecting is by a TAQMAN® assay.

In some embodiments, a method may comprise determining the presence of *Listeria* species other than *Listeria grayi* in a sample. An example of such a method may comprise combining the sample with a culture medium for enriching *Listeria* species for a time to generate a sample enriched for said species; extracting nucleic acid from at least some of the enriched sample; contacting the extracted nucleic acid with at least one primer pair, having a forward and a reverse primer, such as SEQ ID NO:2 and SEQ ID NO:3, or SEQ ID NO:8 and SEQ ID NO:9, or SEQ ID NO:11 and SEQ ID NO:12, or SEQ ID NO:14 and SEQ ID NO:15, or SEQ ID NO:17 and SEQ ID NO:18, or SEQ ID NO:20 and SEQ ID NO:21, or SEQ ID NO:22 and SEQ ID NO:23, or SEQ ID NO:25 and SEQ ID NO:26, or SEQ ID NO:28 and SEQ ID NO:29, or a nucleic acid molecule with at least 90% sequence homology to said SEQ ID sequences, under conditions to generate amplified nucleic acid; and detecting at least some of the amplified nucleic acid, thereby determining the presence of *Listeria* species other than *Listeria* grayi in the sample. In some embodiments of this method, the detecting at least some of the amplified nucleic acid may comprise contacting the amplified nucleic acid with a probe such as described in Table 1 in FIG. 1 corresponding to a selected primer pair, e.g., probe having SEQ ID NO: 4 may be used for detecting an amplified product amplified by a primer pair having SEQ ID NO:2 and SEQ ID NO:3. In some embodiments the probe may be a TAQMAN® probe.

Another method embodiment comprises a method for determining the presence of *Listeria grayi* in a sample is provided, comprising combining the sample with a culture medium for enriching *Listeria* species for a time to generate a sample enriched for said species; extracting nucleic acid from at least some of the enriched sample; contacting the extracted nucleic acid with SEQ ID NO:5 and SEQ ID NO:6, or SEQ ID NO:31 and SEQ ID NO:32, or SEQ ID NO:34 and SEQ ID NO:35, or SEQ ID NO: 37 and SEQ ID NO:38, or SEQ ID NO:40 and SEQ ID NO:41, or SEQ ID NO:43 and SEQ ID NO:44, or SEQ ID NO:46 and SEQ ID NO:47, or a nucleic acid molecule with at least 90% sequence homology to said SEQ ID sequences, under conditions to generate amplified nucleic acid; and detecting at least some of the amplified nucleic acid, thereby determining the presence of *Listeria grayi* in the sample. In some embodiments of this method, the detecting at least some of the amplified nucleic acid may comprise contacting the amplified nucleic acid with a probe such as described in Table 1 in FIG. 1 corresponding to a selected primer pair, e.g., probe having SEQ ID NO: 7 may be used for detecting an amplified product amplified by a primer pair having SEQ ID NO:5 and SEQ ID NO:6. In some embodiments the probe may be a TAQMAN® probe.

Some method embodiments described herein provide highly specific duplexed assays (e.g., TaqMan® real-time PCR assays) that provide for detection of the conserved rnpB gene in *L. monocytogenes, L. innocua, L. ivanovii, L. welshimerii, L. marthii* and *L. seeligeri* as well as the more divergent *L. grayi*, in a single reaction.

A duplexed assay of the disclosure refers to a primer/probe set that is designed to amplify a portion of the rnpB gene of *Listeria* species other than *L. grayi* in combination with a primer/probe set that is designed to amplify a portion of the rnpB gene of *L. grayi*. The duplexed assay embodiments were demonstrated to provide for detection of all *Listeria* species tested and did not detect any non-*Listeria* species, including *Salmonella, Staphylococcus, Streptococcus, Bacillus* and *Escherichia coli*, even at $10^9$ cfu/ml. The PCR efficiency was close to 100% with a limit of detection at 10 genomic copies.

A duplexed assay may be described as a method for determining the presence of *Listeria* species including *Listeria grayi* in a sample comprising: combining the sample with a culture medium for enriching *Listeria* species for a time to generate a sample enriched for said species; extracting nucleic acid from at least some of the enriched sample; contacting the extracted nucleic acid with at least one first primer pair selected from SEQ ID NO:2 and SEQ ID NO:3, or SEQ ID NO:8 and SEQ ID NO:9, or SEQ ID NO:11 and SEQ ID NO:12, or SEQ ID NO:14 and SEQ ID NO:15, or SEQ ID NO:17 and SEQ ID NO:18, or SEQ ID NO:20 and SEQ ID NO:21, or SEQ ID NO:22 and SEQ ID NO:23, or SEQ ID NO:25 and SEQ ID NO:26, or SEQ ID NO:28 and SEQ ID NO:29, or a nucleic acid molecule with at least 90% sequence homology to said first primer pair sequences, under conditions to generate an first amplified nucleic acid; detecting at least some of the first amplified nucleic acid, thereby determining the presence of *Listeria* species other than *Listeria grayi* in the sample; contacting the extracted nucleic acid with at least a second primer pair selected from SEQ ID NO:5 and SEQ ID NO:6, or SEQ ID NO:31 and SEQ ID NO:32, or SEQ ID NO:34 and SEQ ID NO:35, or SEQ ID NO: 37 and SEQ ID NO:38, or SEQ ID NO:40 and SEQ ID NO:41, or SEQ ID NO:43 and SEQ ID NO:44, or SEQ ID NO:46 and SEQ ID NO:47, or a nucleic acid molecule with at least 90% sequence homology to said second primer pair sequences, under conditions to generate a second amplified nucleic acid; and detecting at least some of the second amplified nucleic acid, thereby determining the presence of *Listeria grayi* in the sample.

In the method described above, detecting the first amplified nucleic acid is indicative of the presence of one or more Listeria spp. including *L. monocytogenes, L. innocua, L. welshimeri, L. seelgeri, L. marthii* (formerly *incertae-sedis*), and *L. ivanovii*.

In the method described above, detecting the second amplified nucleic acid is indicative of the presence of *L. grayi*.

In the method described above, the steps of contacting the sample with the first primer pair and contacting the sample with the second primer pair may be simultaneous or sequential. Performing the steps simultaneously and detection of any amplified product may be indicative of the presence of a *Listeria* species in the sample including one or more *Listeria* organisms including *L. monocytogenes, L. innocua, L. welshimeri, L. seelgeri, L. marthii* (formerly *incertae-sedis*), *L. ivanovii*, and *L. grayi*.

Example duplexed assays were evaluated for detection of *Listeria* species from food and environmental samples as provided in Example 4 herein. Experiments with 25 g food samples (smoked salmon, roast beef, hot dogs, infant formula and milk) spiked with 1-3 cfu of bacteria showed also 100% correlation between *Listeria* species detection using real-time PCR and the control culture confirmation method. Robust detection of *Listeria* species from environmental surfaces (ceramic, stainless steel, plastic, rubber and sealed concrete) spiked with 100 cfu of bacteria was observed, with perfect correlation with a control culture confirmation method.

Detection using the real-time PCR assay reduced the time-to-result to less than 27 hours, while allowing for sensitive detection from the complex food and environmental samples. The streamlined workflow offers a great advantage over existing culture confirmation methods by reducing the time-to-result to under 3 h following pre-enrichment. Traditional culture confirmation can take up to a week.

The robustness of the assays and methods of the disclosure allows for addition of more sample volume. Therefore, further embodiments include a step of pooling samples to be tested prior to using a duplexed assay described herein.

The disclosure also describes several kit embodiments for detecting one or more *Listeria* species or strains and may comprise at least one primer pair having hybridization specificity for amplifying a rnpB gene of the one or more *Listeria* species, or for amplifying a fragment of the rnpB gene of *Listeria* species.

In some embodiments, a kit of the disclosure may be created by lyophilizing reagents for a real-time PCR assay (such as primer sequences and optionally probe sequences) together with reagents of a PCR master mix. Kits having these features provide a convenient format since use of such a kit merely requires the addition of sample to the lyophilized kit reagent.

In one embodiment, a kit may be a kit for detection of *Listeria grayi*. An example kit for detecting *Listeria grayi* may comprise a primer pair of isolated nucleic acid molecules having SEQ ID NO:5 and SEQ ID NO:6; or SEQ ID NO:31 and SEQ ID NO:32; or SEQ ID NO:34 and SEQ ID NO:35; or SEQ ID NO: 37 and SEQ ID NO:38; or SEQ ID NO:40 and SEQ ID NO:41; or SEQ ID NO:43 and SEQ ID NO:44; or SEQ ID NO:46 and SEQ ID NO:47; or a nucleic acid molecule with at least 90% sequence homology to said SEQ ID NOs described; or a labeled derivatives thereof; or various combinations of said primer pairs that are operable to amplify a rnpB gene of *Listeria grayi*, or to amplify a fragment of the rnpB gene of *Listeria* grayi.

In one embodiment, a kit may be a kit for detection of a variety of *Listeria* spp. (including for example, *L. monocytogenes, L. innocua, L. ivanovii, L. welshimerii, L. marthii* and *L. seeligeri*). An example kit for detecting *Listeria* spp may comprise a primer pair of isolated nucleic acid molecules having a primer pair having hybridization specificity for amplifying a conserved rnpB gene of *Listeria* species or a fragment thereof, such as SEQ ID NO:1 or a fragment thereof. An exemplary kit for amplifying SEQ ID NO: 1 or a fragment thereof may comprise a primer pair comprising isolated nucleic acid sequences having SEQ ID NO:2 and SEQ ID NO:3, or a nucleic acid molecule with at least 90% sequence homology to said SEQ ID sequences, or a labeled derivative thereof. This kit embodiment may further comprise an isolated nucleic acid molecule consisting of SEQ ID NO:4, or a nucleic acid molecule with at least 90% sequence homology to said SEQ ID sequence, or a labeled derivative thereof, which may be further used as a probe for detecting amplified SEQ ID NO: 1 or a fragment thereof.

In other kit embodiments, the primer pair having hybridization specificity for amplifying a rnpB gene of *Listeria* species, or for amplifying a fragment of the rnpB gene of *Listeria* species, comprises isolated nucleic acid sequences consisting of SEQ ID NO:8 and SEQ ID NO:9, or SEQ ID NO:11 and SEQ ID NO:12, or SEQ ID NO:14 and SEQ ID NO:15, or SEQ ID NO:17 and SEQ ID NO:18, or SEQ ID NO:20 and SEQ ID NO:21, or SEQ ID NO:22 and SEQ ID NO:23, or SEQ ID NO:25 and SEQ ID NO:26, or SEQ ID NO:28 and SEQ ID NO:29, or a nucleic acid molecule with at least 90% sequence homology to said SEQ ID sequences.

The kit may comprise isolated nucleic acid molecules consisting of SEQ ID NO:5 and SEQ ID NO:6, and the kit may further comprise an isolated nucleic acid molecule consisting of SEQ ID NO:7, or a nucleic acid molecule with at least 90% sequence homology to said SEQ ID sequences. In one embodiment, the primer pair has hybridization specificity for amplifying SEQ ID NO:1, or a fragment thereof, and comprises isolated nucleic acid sequences consisting of SEQ ID NO:2 and SEQ ID NO:3, and wherein the kit further comprises isolated nucleic acid molecules consisting of SEQ ID NO:5, SEQ ID NO:6, and SEQ ID NO:7, or a nucleic acid molecule with at least 90% sequence homology to said SEQ ID sequences.

In an embodiment, a kit comprises isolated nucleic acid molecules consisting of SEQ ID NO:2, SEQ ID NO:3, and SEQ ID NO:4, or a nucleic acid molecule with at least 90% sequence homology to said SEQ ID sequences. In a further embodiment, a kit comprises isolated nucleic acid molecules consisting of SEQ ID NO:5, SEQ ID NO:6, and SEQ ID NO:7, or a nucleic acid molecule with at least 90% sequence homology to said SEQ ID sequences.

Kit embodiments may further comprise one or more of these reagents such as at least one of a DNA polymerase, dNTP's, a filtration medium, a surfactant, a buffer, a column, a spin column, a particle and/or magnetic beads, PCR reagents.

These and other features of the present teachings will become more apparent from the description herein.

BRIEF DESCRIPTION OF DRAWINGS

The skilled artisan will understand that the drawings, described below, are for illustration purposes only. The drawings are not intended to limit the scope of the present teachings in any way.

FIG. 1 describes isolated nucleic acid sequences for *Listeria* detection as described herein. The term "FORSEQ" represents the sequence of a forward primer, the term "REVSEQ" represents the sequence of a reverse primer, and the term "PROBESEQ" represents the sequence of a TAQ- MAN® probe. The term "TARGET" refers to a sequence of the rnpB gene of *Listeria* to which a forward primer, reverse primer, or a probe sequence can bind under physiological conditions.

FIG. 3A-FIG. 3D provide data demonstrating assay efficiencies of 100%±10% using serially diluted *L. monocytogenes* (FIG. 3A and FIG. 3B) and *L. grayi* (FIG. 3C and FIG. 3D) genomic DNA. Assay efficiency is determined by the slope and a value of 3.3 represents a ten-fold difference in target concentration. The assays exhibited 100±10% efficiency over a 5 log range of target concentrations.

FIGS. 5A-5D show results of a methods comparison study for comparing the ability of a kit of the disclosure to a reference method of the disclosure for detection of *Listeria* species spiked into food and environmental surfaces

DETAILED DESCRIPTION OF VARIOUS EMBODIMENTS

Figure 2:
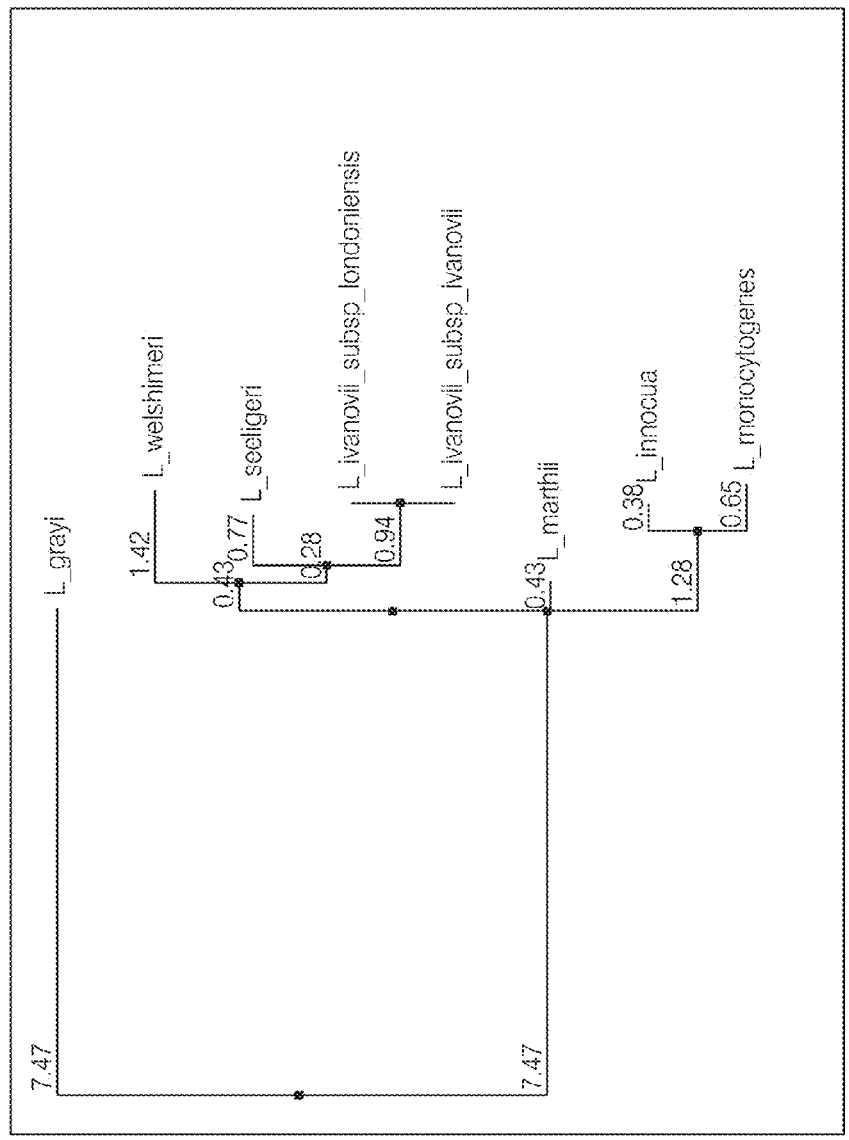
FIG. 2 shows the phlyogenetic tree for gene rnpB, a target for *Listeria* spp. detection methods described herein.

It is to be understood that both the foregoing general description and the following detailed description are exemplary and explanatory only and are not intended to limit the scope of the current teachings. In this application, the use of the singular includes the plural unless specifically stated otherwise. Also, the use of "comprise", "contain", and "include", or modifications of those root words, for example but not limited to, "comprises", "contained", and "including", are not intended to be limiting. Use of "or" means "and/or" unless stated otherwise. The term "and/or" means that the terms before and after can be taken together or separately. For illustration purposes, but not as a limitation, "X and/or Y" can mean "X" or "Y" or "X and Y".

Whenever a range of values is provided herein, the range is meant to include the starting value and the ending value and any value or value range there between unless otherwise specifically stated. For example, "from 0.2 to 0.5" means 0.2, 0.3, 0.4, 0.5; ranges there between such as 0.2-0.3, 0.3-0.4, 0.2-0.4; increments there between such as 0.25, 0.35, 0.225, 0.335, 0.49; increment ranges there between such as 0.26-0.39; and the like.

The section headings used herein are for organizational purposes only and are not to be construed as limiting the subject matter described in any way. All literature and similar materials cited in this application including, but not limited to, patents, patent applications, articles, books, treatises, and internet web pages, regardless of the format of such literature and similar materials, are expressly incorporated by reference in their entirety for any purpose. In the event that one or more of the incorporated literature and similar materials defines or uses a term in such a way that it contradicts that term's definition in this application, this application controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context. The term "surrogate" as used herein means a product that is indicative of presence of another product. For example, an amplification product is a surrogate for a nucleic acid that has been amplified.

Various embodiments herein provide compositions, methods and kits for detection of *Listeria* species and strains, such as *L. monocytogenes, L. innocua, L. ivanovii, L. welshimerii, L. marthii, L. seeligeri* as well as the more divergent *L. grayi*.

The complete genomic sequences of seven *Listeria* strains were determined by the SOLiD™ system (Applied Biosystems, Foster City Calif.) and together with publicly available data, a target gene specific for *Listeria* spp. (and absent in other organisms) was identified. This target gene is the rnpB gene, i.e., the RNase P gene. FIG. 2 shows the phlyogenetic tree for the gene rnpB in various *Listeria* organisms.

FIG. 1 described several isolated nucleic acid sequences of the disclosure identified as SEQ ID NOs:1-48. Of these, SEQ ID NO: 1 comprises a conserved nucleic acid sequence of the rnpB gene of several *Listeria* spp.

The term "TARGET" in Table 1 of FIG. 1 refers to a sequence of the rnpB gene of a *Listeria* organism to which a forward primer, reverse primer, or a probe sequence can bind to under suitable conditions. One example of a TARGET is the nucleic acid comprised in SEQ ID NO: 1. The present disclosure, in some embodiments, relates to isolated nucleic acid molecules having: the sequence of SEQ ID NO: 1, and/or at least 90% homology with SEQ ID NO:1, and/or an at least 10 nucleotide fragment of SEQ ID NO: 1, and/or complementary sequences thereof or a labeled derivative thereof.

The present disclosure in some embodiments describes designing probes and primers for identification and detection of *Listeria* specific target genes or fragments. Some exemplary primer and probe sequences were designed using a rigorous bioinformatics assay design pipeline and are described in FIG. 1 as SEQ ID NO: 2-SEQ ID NO: 48. For example, Table 1 in FIG. 1 describes several primer pairs, comprising at least a first primer referred to as a forward primer and a second primer referred to as a reverse primer. In a row of Table 1, each primer pair also has a corresponding probe sequence. The terms in FIG. 1 "FORSEQ" represents the sequence of a forward primer, "REVSEQ" represents the sequence of a reverse primer, and "PROBESEQ" represents the sequence of a probe (such as for example a TAQMAN® probe).

Compositions of the disclosure comprise primer pairs (and in some embodiments, corresponding probes) that may be used in assays for specific and efficient detection of *Listeria* organisms in samples.

Some compositions of the disclosure may comprise a duplexed set of primer pairs and probes for detection of *Listeria* species in a single assay. For example, a composition may comprise, at least two sets of primer pairs, a first primer set comprising a first primer (a first forward primer)

and a second primer (a first reverse primer) and a second primer set comprising a first primer (a second forward primer) and a second primer (a second reverse primer), each primer set operable to amplify a different target gene or target nucleic acid fragment. The composition may also have a corresponding probe sequence that can hybridize to amplified target nucleic acids of each primer set (a first probe and a second probe). A duplexed primer set may be operable to amplify at least two different target nucleic acid sequences and their corresponding probes are operable to identify at least two different target nucleic acid sequences. Compositions of the disclosure may comprise additional primer pairs (such as three primer pairs, four primer pairs and optionally the same number of corresponding probes as well).

Further compositions of the disclosure may comprise at least one set of primer pair and probe sequences for distinguishing *L. grayi* from other *Listeria* species.

In some embodiments, the disclosure describes methods of detecting in a sample the presence of *Listeria* spp and/or methods for detecting and identifying certain *Listeria* species and/or strains and/or serotypes.

In some embodiments, a method of the disclosure, may comprise detecting, in a sample, at least one (or more) nucleic acid sequence(s) having at least 10 to at least 25 nucleic acids of SEQ ID NO:1 and/or complementary sequences thereof, wherein detection of at least one nucleic acid sequence indicates the presence of an *Listeria* organism in the sample. In some embodiments this method may comprise detecting a *Listeria* organism of the species *L. monocytogenes, L. innocua, L. ivanovii, L. welshimerii, L. marthii* and/or *L. seeligeri*. In some embodiments this method may comprise detecting a *Listeria* organism that is not *Listeria grayi*.

Methods of detection may further comprise steps of sample preparation and may also comprise identification steps (to identify a species/strain). Such embodiments are described in detail in sections below.

In some embodiments, a method of the disclosure may further comprise preparing a sample for PCR amplification (prior to hybridizing with a primer pair), for example, but not limited to (1) bacterial enrichment, (2) separation of bacterial cells from the sample, (3) cell lysis, and (4) nucleic acid extraction (e.g. total DNA, genomic DNA).

Samples may include without limitation, clinical samples, food/beverage samples, water samples, and environmental sample. Food sample may comprise raw produce, meats as well as a selectively enriched food matrix.

In some embodiments, a method for the detection of a *Listeria* spp. in a sample comprising a) hybridizing a first pair of PCR primers comprising a forward primer and a reverse primer (e.g., selected for example from a row in Table 1 shown in FIG. 1) that are operable to bind to and amplify a rnpB gene or fragment thereof found only in *Listeria* spp and not in other organisms; b) amplifying the rnpB gene or fragment thereof found only in *Listeria* spp and not in other organisms to form an amplified target nucleic acid product; and d) detecting the amplified target polynucleotide sequence product; wherein the detection of the amplified target polynucleotide sequence product is indicative of the presence of *Listeria* spp. in the sample.

Methods of the disclosure may include assays such as polymerase chain reactions, wherein hybridizing and amplifying of said first pair of polynucleotide primers occurs in a first vessel and said hybridizing and amplifying of said second pair of polynucleotide primers occurs in a second vessel, or hybridizing and amplifying of said first pair of polynucleotide primers and said hybridizing and amplifying of said second pair of polynucleotide primers occurs in a single vessel. The detection may be a real-time assay and the real-time assay may be a SYBR® Green dye assay or a TaqMan® assay.

Detection may be performed by a variety of methods, such as but not limited to, by a nucleic acid amplification reaction. The amplification reaction may be an end-point determination, the amplification reaction maybe quantitative, the quantification maybe a real-time PCR, the real-time PCR maybe a SYBR® Green Assay, and/or the real-time PCR may be a TaqMan® Assay. Detection in some embodiments may be performed by hybridization using probes specific to target sequences. Combinations of amplification and hybridization may be used for detection according to some embodiments.

Methods of the disclosure, in various embodiments, may comprise providing a first probe and a second probe the probes, wherein the first and second probes are different from each other, the first probe operable to identify the first amplified target polynucleotide sequence and the second probe operable to identify the second amplified target nucleotide sequence, the first probe further comprises a first label and said second probe further comprises a second label, wherein both labels are selected from a dye, a radioactive isotope, a chemiluminescent label, and an enzyme, the dye comprises a fluorescein dye, a rhodamine dye, or a cyanine dye, the dye is a fluorescein dye and first probe is labeled with FAM™ dye and said second probe is labeled with VIC® dye; and hybridizing the first and second probes to the PCR amplified fragments to detect the presence of the first amplified target polynucleotide sequence and the second amplified target polynucleotide sequence from the sample.

In one embodiments, a method for determining the presence of a *Listeria* species in a sample comprises combining the sample with a culture medium for enriching *Listeria* species for a time to generate a sample enriched for said species; extracting nucleic acid from at least some of the enriched sample; contacting the extracted nucleic acid with at least one primer pair having hybridization specificity for amplifying a rnpB gene of *Listeria* species, or a fragment of the rnpB gene of *Listeria* species comprising a primer pair having SEQ ID NO:5 and SEQ ID NO:6, or SEQ ID NO:31 and SEQ ID NO:32, or SEQ ID NO:34 and SEQ ID NO:35, or SEQ ID NO: 37 and SEQ ID NO:38, or SEQ ID NO:40 and SEQ ID NO:41, or SEQ ID NO:43 and SEQ ID NO:44, or SEQ ID NO:46 and SEQ ID NO:47, or a nucleic acid molecule with at least 90% sequence homology to said SEQ ID sequences under conditions to generate amplified nucleic acid; and detecting at least some of the amplified nucleic acid, thereby determining the presence of *Listeria* species in the sample. In some embodiments, at least two of the above referenced primer pairs may be used.

In some embodiments, a primer pair having hybridization specificity for amplifying a rnpB gene of *Listeria* species, or for amplifying a fragment of the rnpB gene of *Listeria* species, amplifies SEQ ID NO:1 or a fragment thereof. In some embodiments, a primer pair having hybridization specificity for amplifying SEQ ID NO:1, or a fragment thereof, comprises isolated nucleic acid sequences having SEQ ID NO:2 and SEQ ID NO:3, or a nucleic acid molecule with at least 90% sequence homology to said SEQ ID sequences or a labeled derivative thereof. In further embodiments, the conditions to generate amplified nucleic acid further include an isolated nucleic acid molecule consisting of SEQ ID NO:4, or a nucleic acid molecule with at least 90% sequence homology to said SEQ ID sequence or a labeled derivative thereof.

In further method embodiments, a primer pair having hybridization specificity for amplifying a rnpB gene of *Listeria* species, or for amplifying a fragment of the rnpB gene of *Listeria* species, comprises isolated nucleic acid sequences consisting of SEQ ID NO:8 and SEQ ID NO:9, or SEQ ID NO:11 and SEQ ID NO:12, or SEQ ID NO:14 and SEQ ID NO:15, or SEQ ID NO:17 and SEQ ID NO:18, or SEQ ID NO:20 and SEQ ID NO:21, or SEQ ID NO:22 and SEQ ID NO:23, or SEQ ID NO:25 and SEQ ID NO:26, or SEQ ID NO:28 and SEQ ID NO:29, or a nucleic acid molecule with at least 90% sequence homology to said SEQ ID sequences or a labeled derivative thereof. In certain embodiments, the extracted nucleic acid is contacted with isolated nucleic acid molecules having SEQ ID NO:2, SEQ ID NO:3, SEQ ID NO:5, and SEQ ID NO:6, or a nucleic acid molecule with at least 90% sequence homology to said SEQ ID sequence or a labeled derivative thereof. In some embodiments, the contacting includes contacting with 5'-labeled isolated nucleic acids SEQ ID NO:4 and SEQ ID NO:7, or a nucleic acid molecule with at least 90% sequence homology to said SEQ ID sequence. In some embodiments, the detecting is by a TAQMAN® assay.

In some embodiments, a method may comprise determining the presence of *Listeria* species other than *Listeria grayi* in a sample. An example of such a method may comprise combining the sample with a culture medium for enriching *Listeria* species for a time to generate a sample enriched for said species; extracting nucleic acid from at least some of the enriched sample; contacting the extracted nucleic acid with at least one primer pair, having a forward and a reverse primer, such as SEQ ID NO:2 and SEQ ID NO:3, or SEQ ID NO:8 and SEQ ID NO:9, or SEQ ID NO:11 and SEQ ID NO:12, or SEQ ID NO:14 and SEQ ID NO:15, or SEQ ID NO:17 and SEQ ID NO:18, or SEQ ID NO:20 and SEQ ID NO:21, or SEQ ID NO:22 and SEQ ID NO:23, or SEQ ID NO:25 and SEQ ID NO:26, or SEQ ID NO:28 and SEQ ID NO:29, or a nucleic acid molecule with at least 90% sequence homology to said SEQ ID sequences, under conditions to generate amplified nucleic acid; and detecting at least some of the amplified nucleic acid, thereby determining the presence of *Listeria* species other than *Listeria* grayi in the sample. In some embodiments of this method, the detecting at least some of the amplified nucleic acid may comprise contacting the amplified nucleic acid with a probe such as described in Table 1 in FIG. 1 corresponding to a selected primer pair, e.g., probe having SEQ ID NO: 4 may be used for detecting an amplified product amplified by a primer pair having SEQ ID NO:2 and SEQ ID NO:3. In some embodiments the probe may be a TAQMAN® probe.

Another method embodiment comprises a method for determining the presence of *Listeria grayi* in a sample is provided, comprising combining the sample with a culture medium for enriching *Listeria* species for a time to generate a sample enriched for said species; extracting nucleic acid from at least some of the enriched sample; contacting the extracted nucleic acid with SEQ ID NO:5 and SEQ ID NO:6, or SEQ ID NO:31 and SEQ ID NO:32, or SEQ ID NO:34 and SEQ ID NO:35, or SEQ ID NO: 37 and SEQ ID NO:38, or SEQ ID NO:40 and SEQ ID NO:41, or SEQ ID NO:43 and SEQ ID NO:44, or SEQ ID NO:46 and SEQ ID NO:47, or a nucleic acid molecule with at least 90% sequence homology to said SEQ ID sequences, under conditions to generate amplified nucleic acid; and detecting at least some of the amplified nucleic acid, thereby determining the presence of *Listeria grayi* in the sample. In some embodiments of this method, the detecting at least some of the amplified nucleic acid may comprise contacting the amplified nucleic acid with a probe such as described in Table 1 in FIG. 1 corresponding to a selected primer pair, e.g., probe having SEQ ID NO: 7 may be used for detecting an amplified product amplified by a primer pair having SEQ ID NO:5 and SEQ ID NO:6. In some embodiments the probe may be a TAQMAN® probe.

Some method embodiments described herein provide highly specific duplexed assays (e.g., TaqMan® real-time PCR assays) that provide for detection of the conserved rnpB gene in *L. monocytogenes, L. innocua, L. ivanovii, L. welshimerii, L. marthii* and *L. seeligeri* as well as the more divergent *L. grayi*, in a single reaction.

A duplexed assay of the disclosure refers to a primer/probe set that is designed to amplify a portion of the rnpB gene of *Listeria* species other than *L. grayi* in combination with a primer/probe set that is designed to amplify a portion of the rnpB gene of *L. grayi*. The duplexed assay embodiments were demonstrated to provide for detection of all *Listeria* species tested and did not detect any non-*Listeria* species, including *Salmonella, Staphylococcus, Streptococcus, Bacillus* and *Escherichia coli*, even at $10^9$ cfu/ml. The PCR efficiency was close to 100% with a limit of detection at 10 genomic copies.

Several compositions of the disclosure comprising primer pair and probe sets have been assayed for specificity and efficiency in detection of *Listeria*. *Listeria* detection methods described here have been tested in a wide variety samples. *Listeria* spp are known to be present in food samples, in samples from the environment, or from animal or humans who are potential carriers. A sample for detection of *Listeria* species may be an uncooked food sample such as uncooked meats, fish, poultry vegetables, unpasteurized milk, foods made from unpasteurized milk, or dairy products, or cooked or processed foods such as hot dogs, deli meats, cheeses, poultry, ice cream, smoked fish, or seafood, for example; an environmental sample for detection of *Listeria* species may be soil, stream water, sewage, plants, or swabs from food processing equipment, or any surface that is involved with food processing.

Typically a portion of food or a swabbed sample is combined with an appropriate liquid, such as water, a buffer solution, or a culture medium such as a selective medium or an enrichment medium. In some embodiments, food is chopped, macerated, liquefied, diced, or homogenized. In some embodiments, large volumes of sample, for example, but not limited to, volumes of 100 mL, 250 mL, or more are processed or a portion of the food or beverage and appropriate liquid are typically combined to form a dilute suspension, for example but not limited to, ratios of about 1:5, 1:10, or 1:20 (w/vol). In some embodiments, a detergent, an emulsifying agent, or both, is added to enhance the solubility of high lipid foods, for example but not limited to butter and certain other dairy products. In certain embodiments, 25 grams of a solid or semi-solid food is combined with 225 mL of a suitable culture media. In some embodiments, 25 mL of a beverage or a liquefied or partially liquefied food is combined with 225 mL of a suitable culture media.

Samples may also be pooled to save on testing costs, e.g., instead of testing 15×25 g samples of food, a composite of 375 g, with 25 g coming from different lots of food are tested. If any composite is tested positive, then the individual 15 samples are further evaluated. If the composite is negative, then the food testing lab has saved the cost of 15 individual tests.

Solid samples (e.g., 25 g), liquid samples (e.g., 10 ml-100 ml) or swabbed samples (resuspended in e.g., 10 ml-100 ml) can be pre-enriched for *Listeria* species for ~4 h in buffered *Listeria* enrichment broth (BLEB), or an equivalent thereof. After 4 hours of incubation, *Listeria* selective agents are added (see e.g., Example 4 herein). Alternative enrichment media include Tryptic Soy Broth, Brain Heart Infusion Broth or Fraser Broth, for which ingredients can be found in, for example, "Compendium of Methods for the Microbiological Examination of Foods," 4th Edition (2001) Downes and Ito, eds. American Public Health Association, or U.S. Food and Drug Administration Bacteriological Analytical Manual (BAM), Media Index on the FDA web site. Incubation for selective enrichment is continued for a total of 24 hours enrichment, or may be continued for up to 48 h.

The entire volume of the enriched culture, or a portion thereof, may be concentrated and processed for detection of *Listeria* spp, for example, a one mL aliquot may be taken from 250 mL of enriched culture. The medium may be clarified by filtration prior to or after concentrating. Harvested samples are lysed using, for example, the PrepSEQ™ Nucleic Acid Extraction Kit (Applied Biosystems) or the PrepSEQ™ RapidSpin Kit (Applied Biosystems) or any other effective lysis system that preserves nucleic acid integrity. The lysate can be amplified directly or the nucleic acid can be extracted and amplified using the *Listeria* spp PCR primers provided herein. Amplification products are detected, directly or indirectly, and the presence or absence of *Listeria* spp in the sample can be determined.

High quality DNA can be prepared by manual low throughput methods or by automated high throughput methods, depending on the number of samples being tested. An integrated workflow for automated high-throughput sample preparation may include food enrichment for *Listeria* spp., lysis, binding of nucleic acids to magnetic particles, magnetic separation, followed by optional washes and elution of DNA in a PCR compatible solution. Another integrated workflow for automated high-throughput sample preparation may include food enrichment for *Listeria* spp., lysis, binding of nucleic acids to particles or to columns (such as spin columns), separation, of nucleic acids from the particles or columns; followed by optional washes and elution of DNA in a PCR compatible solution. An integrated workflow for manual low-throughput sample preparation may include food enrichment for *Listeria* spp., centrifugation to clarify and pellet bacteria, resuspension of bacteria in lysis buffer, followed by amplification using *Listeria* specific PCR as provided herein. The integrated system may also include lyophilized reagents for the assay and data analyses software.

As used herein, "amplification" or "amplify" and the like refers to a process that results in an increase in the copy number of a molecule or set of related molecules. Amplification can encompass a variety of chemical and enzymatic processes including without limitation, a polymerase chain reaction (PCR), a strand displacement amplification reaction, a transcription mediated amplification reaction, a nucleic acid sequence-based amplification reaction, a rolling circle amplification reaction, or a ligase chain reaction. According to certain embodiments, following at least one amplification cycle, the amplification products can be detected by sequence or by separation based on their molecular weight or length or mobility, for example.

PCR includes introducing a molar excess of at least one primer pair (two or more extendable oligonucleotide primers) to a reaction mixture comprising the test *Listeria* nucleic acid sample where the primers hybridize to opposite strands of DNA. The reaction mixture is subjected to a program of thermal cycling in the presence of a DNA polymerase, resulting in the amplification of the DNA sequence flanked by the primers. The reaction mixture is subjected to a program of thermal cycling in the presence of a DNA polymerase, resulting in the amplification of the DNA flanked by the primers.

The sequence-specific portions of the primers are of sufficient length to permit specific annealing to complementary sequences, as appropriate. A primer does not need to have 100% complementarity with its target sequence for primer extension to occur. Further, a primer can be detectably labeled such that the label is detected by, for example, biochemical, chemical, immunochemical, spectroscopic, photochemical, or other detection means. A primer pair includes a "forward primer" and a "reverse primer," indicating that they are initiating nucleic acid polymerization in opposing directions from different strands of a duplex template. In some embodiments, a primer as set forth herein can comprise a priming site common to a subset of *Listeria* species. For example, SEQ ID NO:2 is able to hybridize to a portion of the rnpB gene in *L. monocytogenes, L. innocua, L. ivanovii, L. welshimerii, L. marthii* and *L. seeligeri*.

"Hybridization" refers to a process in which single-stranded nucleic acids with complementary or near-complementary base sequences interact to form hydrogen-bonded complexes called hybrids. Hybridization reactions are sensitive and selective. In vitro, the specificity of hybridization (i.e., stringency) is controlled by the concentrations of salt or formamide in prehybridization and hybridization solutions, for example, and by the hybridization temperature; such procedures are well known in the art. In particular, stringency is increased by reducing the concentration of salt, increasing the concentration of formamide, or raising the hybridization temperature. For example, high stringency conditions could occur at about 50% formamide at 37° C. to 42° C. Reduced stringency conditions could occur at about 35% to 25% formamide at 30° C. to 35° C. Examples of stringency conditions for hybridization are provided in Sambrook, J., 1989, *Molecular Cloning A Laboratory Manual*, Cold Spring Harbor Laboratory Press, Cold Spring Harbor, N.Y. The temperature for hybridization is about 5-10° C. less than the melting temperature (Tm) of the hybrid.

As an example of primer selection, primers can be selected by the use of any of various software programs available and known in the art for developing amplification and/or multiplex systems. Exemplary programs include, PRIMER EXPRESS® software (Applied Biosystems, Foster City, Calif.) and Primer3 software (Rozen S et al. (2000), "Primer3 on the WWW for general users and for biologist programmers," Krawetz S et al. (eds) *Bioinformatics Methods and Protocols: Methods in Molecular Biology*. Humana Press, Totowa, N.J., pp 365-386). In the example of the use of software programs, sequence information from SEQ ID NO:1, for example, can be imported into the software. The software then uses various algorithms to select primers that best meet the user's specifications.

Primer and probe sequences having at least 90% homology to those of SEQ ID NO: 2-SEQ ID NO:48 are some embodiments described herein. "Homology," as known by one of ordinary skill in the art, is the degree of sequence relatedness between nucleotide sequences as determined by matching the order and identity of nucleotides between the sequences. In one embodiment, the primer or probe sequences provided herein have 100% homology, at least 98% homology, at least 95% homology, at least 92% homology or at least 90% homology to SEQ ID NO:2-SEQ ID NO:48. Computer methods for determining homology are designed to identify the greatest degree of matching of nucleotide sequences, for example, BLASTN (Altschul, S. F., et al. (1990) *J. Mol. Biol.* 215:403-410).

In certain embodiments, single-stranded amplification products can be generated by methods including, without limitation, asymmetric PCR, asymmetric reamplification, nuclease digestion, and chemical denaturation. For example, single-stranded sequences can be generated by combining at least one first primer or at least one second primer from a primer set, but not both, in an amplification reaction mixture.

The term "polymerase," as used herein, refers to a polypeptide that is able to catalyze the addition of nucleotides or analogs thereof to a nucleic acid in a template dependent manner, for example, the addition of deoxyribonucleotides to the 3'-end of a primer that is annealed to a nucleic acid template during a primer extension reaction. Nucleic acid polymerases can be thermostable or thermally degradable. Suitable thermostable polymerases include, but are not limited to, polymerases isolated from *Thermus aquaticus, Thermus thennophilus, Pyrococcus woesei, Pyrococcus furiosus, Thermococcus litoralis*, and *Thermotoga maritima*. Suitable thermodegradable polymersases include, but are not limited to, *E. coli* DNA polymerase I, the Klenow fragment of *E. coli* DNA polymerase I, T4 DNA polymerase, T5 DNA polymerase, T7 DNA polymerase, and others. Examples of other polymerizing enzymes that can be used in the methods described herein include but are not limited to T7, T3, SP6 RNA polymerases; and AMV, M-MLV and HIV reverse transcriptases.

Commercially available polymerases include, but are not limited to, TAQ DNA polymerase (Invitrogen), PLATINUM®TAQ DNA polymerase (Invitrogen), SUPER-TAQ® polymerase and SUPERTAQ® Plus polymerase, TAQFS® polymerase, AMPLITAQ® CS polymerase (Perkin-Elmer), AMPLITAQ® FS polymerase (Perkin-Elmer), KENTAQ1® polymerase (AB Peptide, St. Louis, Mo.), TAQUENASE® polymerase (Scien Tech Corp., St. Louis, Mo.), THERMOSEQUENASE® polymerase (Amersham), Bst polymerase, READER™Taq DNA polymerase, VENT® DNA polymerase, VENT$_R$® DNA Polymerase, VENT$_R$® (exo⁻) polymerase and DEEPVENT® DNA polymerase, (all VENT® polymerases can be obtained from New England Biolabs), PFUTurbo™ DNA polymerase (Stratagene), Pwo polymerase, Tth DNA polymerase, KlenTaq-1 polymerase, SEQUENASE™ 1.0 DNA polymerase (Amersham Biosciences), SEQUENASE™ 2.0 DNA polymerase (United States Biochemicals), and an enzymatically active mutant and variant thereof.

Descriptions of DNA polymerases can be found in, among other places, Lehninger *Principles of Biochemistry*, 3d ed., Nelson and Cox, Worth Publishing, New York, N.Y., 2000, particularly Chapters 26 and 29; Twyman, *Advanced Molecular Biology: A Concise Reference*, Bios Scientific Publishers, New York, N.Y., 1999; Ausubel et al., *Current Protocols in Molecular Biology*, John Wiley & Sons, Inc., including supplements through May 2005; Lin and Jaysena, *J. Mol. Biol.* 271:100-11, 1997; Pavlov et al., *Trends in Biotechnol.* 22:253-60, 2004; and *Enzymatic Resource Guide: Polymerases*, 1998, Promega, Madison, Wis.

In various detection embodiments, amplification is optionally followed by additional steps, for example, but not limited to, labeling, sequencing, purification, isolation, hybridization, size resolution, expression, detecting and/or cloning. In certain embodiments, one or both PCR primers can comprise a label, such as, for example, a fluorophore. A label can facilitate detection of an amplification product comprising a labeled PCR primer.

As used herein, "real-time PCR" refers to the detection and quantitation of a DNA or a surrogate thereof in a sample. In some embodiments, the amplified segment or "amplicon" can be detected in real time using a 5'-nuclease assay, particularly the TAQMAN® assay as described by e.g., Holland et al. (*Proc. Natl. Acad. Sci. USA* 88:7276-7280, 1991); and Heid et al. (*Genome Research* 6:986-994, 1996). For use herein, a TAQMAN® nucleotide sequence to which a TAQMAN® probe binds can be designed into the primer portion, or known to be present in DNA of a sample.

"$T_m$" refers to the melting temperature (temperature at which 50% of the oligonucleotide is a duplex) of an oligonucleotide determined experimentally or calculated using the nearest-neighbor thermodynamic values of SantaLucia J. et al. (*Biochemistry* 35:3555-62, 1996) for DNA. In general, the $T_m$ of the TAQMAN® probe is about 10 degrees above the $T_m$ of amplification primer pairs. The $T_m$ of the MGB probes is calculated using the SantaLucia method with factors correcting for the increased $T_m$ due to MGB.

When a TAQMAN® probe is hybridized to DNA or a surrogate thereof, the 5'-exonuclease activity of a thermostable DNA-dependent DNA polymerase such as SUPER-TAQ® (a Taq polymerase from *Therms aquaticus*, Ambion, Austin, Tex.) digests the hybridized TAQMAN® probe during the elongation cycle, separating the fluor from the quencher. The reporter fluor dye is then free from the quenching effect of the quencher moiety resulting in a decrease in FRET and an increase in emission of fluorescence from the fluorescent reporter dye. One molecule of reporter dye is generated for each new molecule synthesized, and detection of the free reporter dye provides the basis for quantitative interpretation of the data. In real-time PCR, the amount of fluorescent signal is monitored with each cycle of PCR. Once the signal reaches a detectable level, it has reached the "threshold or cycle threshold (Ct)." A fluorogenic PCR signal of a sample can be considered to be above background if its Ct value is at least 1 cycle less than that of a no-template control sample. The term "Ct" represents the PCR cycle number when the signal is first recorded as statistically significant. Thus, the lower the Ct value, the greater the concentration of nucleic acid target. In the TAQMAN® assay, typically each cycle almost doubles the amount of PCR product and therefore, the fluorescent signal should double if there is no inhibition of the reaction and the reaction was nearly 100% efficient with purified nucleic acid. Certain systems such as the ABI 7500, 7500FAST, 7700 and 7900HT Sequence Detection Systems (Applied Biosystems, Foster City, Calif.) conduct monitoring during each thermal cycle at a pre-determined or user-defined point.

Detection method embodiments using a TAQMAN® probe sequence comprise combining the test sample with PCR reagents, including a primer set having a forward primer and a reverse primer, a DNA polymerase, and a fluorescent detector oligonucleotide TAQMAN® probe, as well as dNTP's and a salt, to form an amplification reaction mixture; subjecting the amplification reaction mixture to successive cycles of amplification to generate a fluorescent signal from the detector probe; and quantitating the nucleic acid presence based on the fluorescent signal cycle threshold of the amplification reaction.

Protocols and reagents for means of carrying out other 5'-nuclease assays are well known to one of skill in the art, and are described in various sources. For example, 5'-nuclease reactions and probes are described in U.S. Pat. No. 6,214,979 issued Apr. 10, 2001; U.S. Pat. No. 5,804,375 issued Sep. 8, 1998; U.S. Pat. No. 5,487,972 issued Jan. 30, 1996; and U.S. Pat. No. 5,210,015 issued May 11, 1993, all to Gelfand et al.

A "label" or "reporter," refers to a moiety or property that allows the detection of that with which it is associated. The label can be attached covalently or non-covalently. Examples of labels include fluorescent labels (including, e.g., quenchers or absorbers), colorimetric labels, chemiluminescent labels, bioluminescent labels, radioactive labels, mass-modifying groups, antibodies, antigens, biotin, haptens, enzymes (including, e.g., peroxidase, phosphatase, etc.), and the like. Fluorescent labels can include dyes that are negatively charged, such as dyes of the fluorescein family including, e.g. FAM™ dye, HEX™ dye, TET™ dye, JOE™ dye, NAN and ZOE; or dyes that are neutral in charge, such as dyes of the rhodamine family including, e.g., TEXAS RED® dye, ROX™ dye, R110, R6G, and TAMRA™ dye; or dyes that are positively charged, such as dyes of the CYANINE™ family including e.g., Cy™2 dye, Cy™3 dye, Cy™5 dye, Cy™5.5 dye and Cy™7 dye. FAM™ dye, HEX™ dye, TET™ dye, JOE™ dye, NAN, ZOE, ROX™ dye, R110, R6G, and TAMRA™ dyes are available from, e.g., Applied Biosystems (Foster City, Calif.) or Perkin-Elmer, Inc. (Wellesley, Mass.); TEXAS RED® dye is available from, e.g., Molecular Probes, Inc. (Eugene, Oreg.); and Cy™2 dye, Cy™3 dye, Cy™5 dye, Cy™5.5 dye and Cy™7 dye, and are available from, e.g., Amersham Biosciences Corp. (Piscataway, N.J.). In certain embodiments, the fluorescer molecule is a fluorescein dye and the quencher molecule is a rhodamine dye.

A label or reporter can comprise both a fluorophore and a fluorescence quencher. The fluorescence quencher can be a fluorescent fluorescence quencher, such as the fluorophore TAMRA™ dye, or a non-fluorescent fluorescence quencher (NFQ), for example, a combined NFQ-minor groove binder (MGB) such as an MGB ECLIPSE™ minor groove binder supplied by Epoch Biosciences (Bothell, Wash.) and used with TAQMAN™ probes (Applied Biosystems, Foster City, Calif.). The fluorophore can be any fluorophore that can be attached to a nucleic acid, such as, for example, FAM™ dye, HEX™ dye, TET™ dye, JOE™ dye, NAN, ZOE, TEXAS RED® dye, ROX™ dye, R110, R6G, TAMRA™ dye, Cy™2 dye, Cy™3 dye, Cy™5 dye, Cy™5.5 dye and Cy™7 dye as cited above as well as VIC® dye, NED™ dye, LIZ® dye, ALEXA, Cy™9 dye, and dR6G.

Further examples of labels include black hole quenchers (BHQ) (Biosearch), Iowa Black (IDT), QSY quencher (Molecular Probes), and Dabsyl and Dabcel sulfonate/carboxylate Quenchers (Epoch).

Labels can also comprise sulfonate derivatives of fluorescein dyes, phosphoramidite forms of fluorescein, phosphoramidite forms of CY™5 (available for example from Amersham), intercalating labels such as ethidium bromide, and SYBR™ Green I dye and PICOGREEN™ dye (Molecular Probes).

Generally, an intercalating label is a molecule that reversibly inserts between two other molecules (or groups) such as between the bases of DNA.

In various embodiments, qPCR reactions can include master mixes such as the TAQMAN® Gene Expression Master Mix, TAQMAN® Universal PCR Master Mix, TAQMAN® Fast Universal PCR Master Mix, Power SYBR® Green PCR Master Mix, Fast SYBR® Green Master Mix, for example, all from Applied Biosystems.

In various embodiments, detection of fluorescence of a PCR assay can be by any method known to skilled artisans, in view of this disclosure, and can include, for example, real time detection as described supra or end point detection. Detection of fluorescence can be qualitative or quantitative. Quantitative results can be obtained, for example, with the aid of a fluorimeter, for example a fluorimeter comprised by an integrated nucleic acid analysis system, such as, for example, an Applied Biosystems ABI PRISM™ 7900HT Sequence Detection System. Furthermore, quantitative results can be obtained in some configurations using a real-time PCR analysis as described supra. Some non-limiting examples of protocols for conducting fluorogenic assays such as TAQMAN® assays, including analytical methods for performing quantitative assays, can be found in publications such as, for example, "SNPLEX™ Genotyping System 48-plex", Applied Biosystems, 2004; "User Bulletin #2 ABI PRISM™ 7700 Sequence Detection System," Applied Biosystems 2001; "User Bulletin #5 ABI PRISM™ 7700 Sequence Detection System," Applied Biosystems, 2001; and "Essentials of Real Time PCR," Applied Biosystems (Foster City, Calif.). Fluorogenic PCR assays used in some configurations of the present teachings can be performed using an automated system, such as, for example, an ABI 7700 Sequence Detection System (Applied Biosystems).

For real time PCR, a passive reference dye, ROX™ dye, can be included in PCR reactions to provide an internal reference to which the reporter-dye signal can be normalized during data analysis. Normalization can be accomplished using Applied Biosystems' Sequence Detection System (SDS) software.

In general for the studies herein, the TAQMAN® probes were labeled with FAM™ dye, the TAQMAN® probe for the Internal Positive Control was labeled with VIC® dye and a Baseline Control was detected using ROX® Dye. Data analyses were carried out using the RAPIDFINDER™ Express Software (Applied Biosystems) and results are provided in an easy-to-read format with present/absent calls.

Figure 3A:
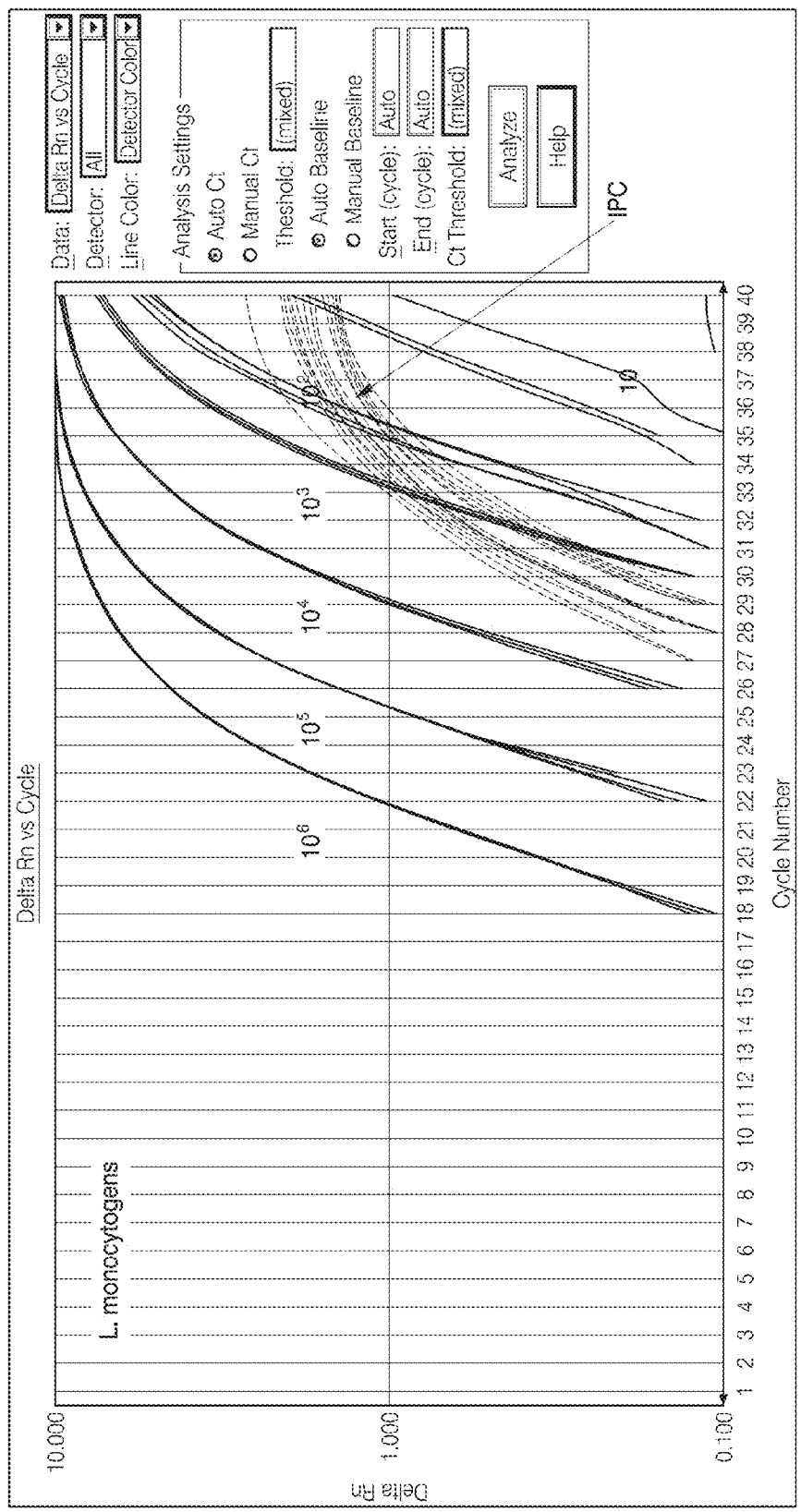
Figure 3C:
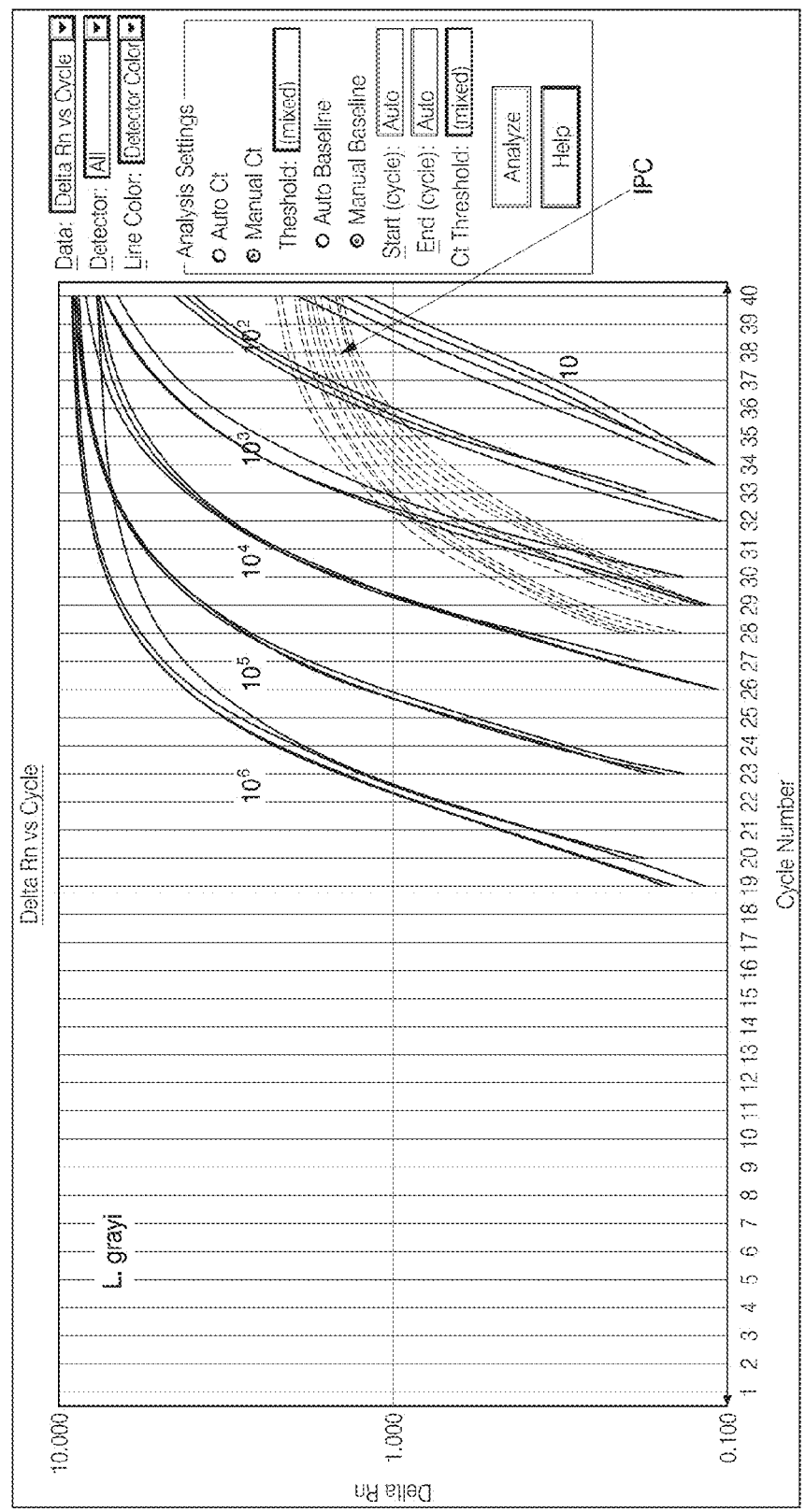
Figure 3D:
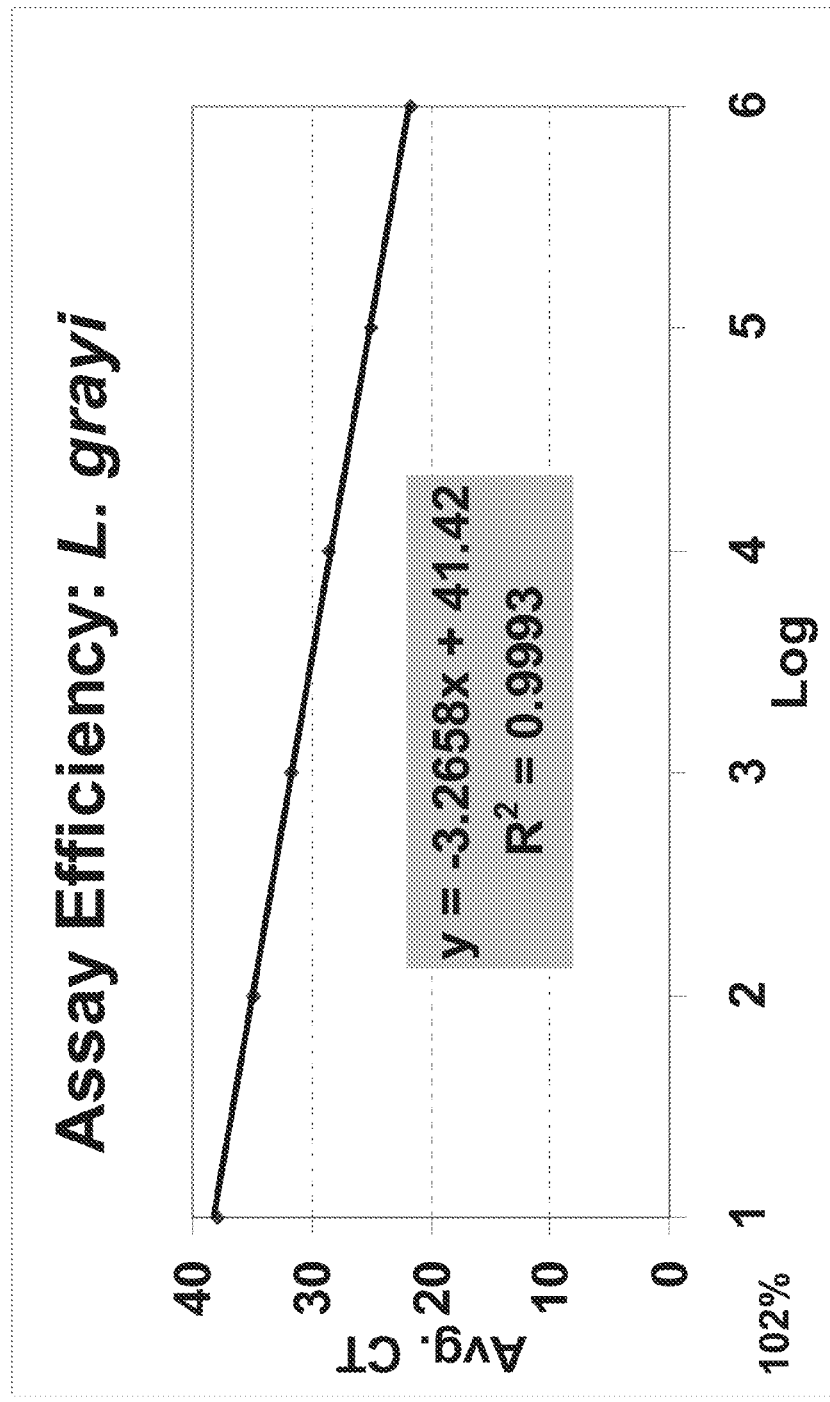

Data demonstrating assay efficiencies for the duplexed *Listeria* spp assay provided herein of 100%±10% using serially diluted *L. monocytogenes* and *L. grayii* genomic DNA are provided by FIG. 3A and FIG. 3B, respectively. Assay efficiency is determined by the slope and a value of 3.3 represents a ten-fold difference in target concentration. The assays exhibited 100±10% efficiency over a 5 log range of target concentrations. The limit of detection is at 10 genomic copies.

Figure 4A:
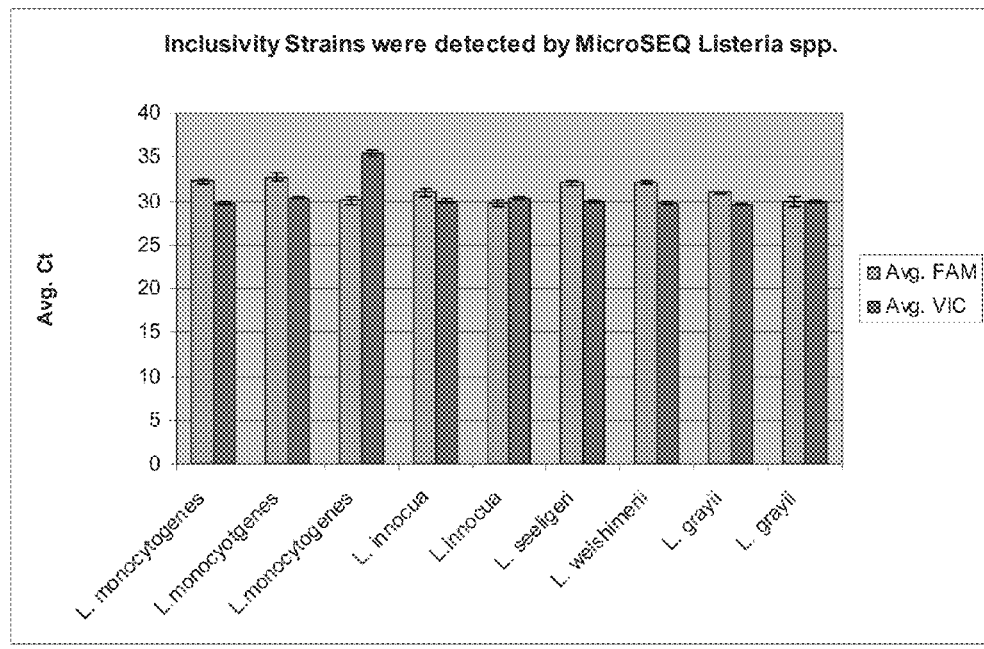
FIG. 4A provides data demonstrating that the *Listeria* spp. duplexed assay showed 100% specificity to all inclusivity targets analyzed.
Figure 4B:
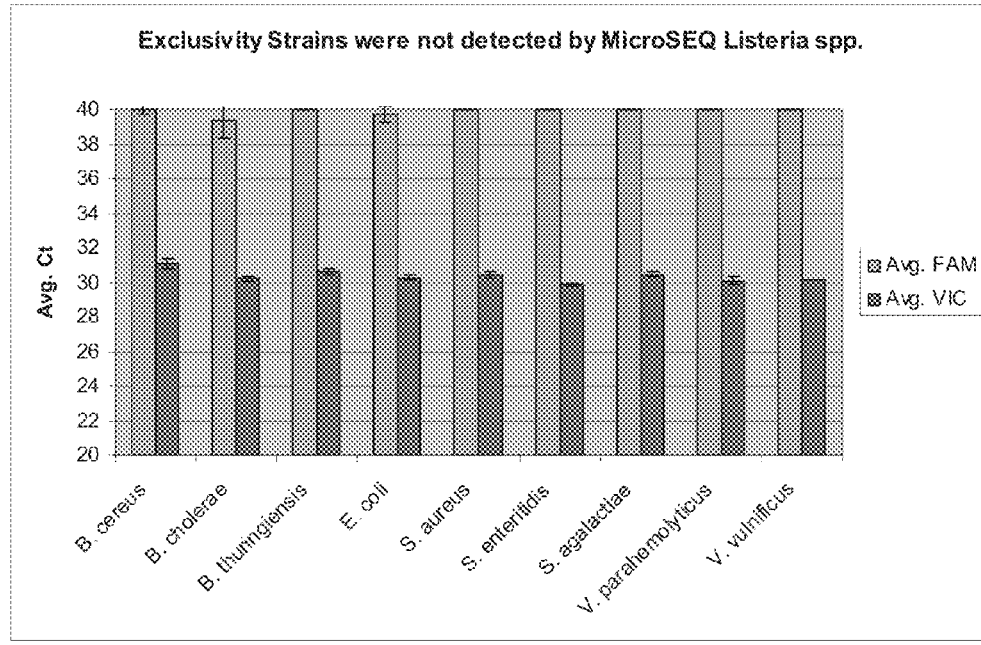
FIG. 4B provides data demonstrating that the cited gram positive and gram negative bacteria were not detected even at $10^9$ cfu/ml using the *Listeria* spp. duplexed assay of embodiments herein.

Data demonstrating that the present *Listeria* spp. duplexed assay showed 100% specificity to all inclusivity targets analyzed are provided by FIG. 4A and data demonstrating that gram positive (e.g., *Staphylococcus aureus, Bacillus* spp. *Streptococcus agalactiae*) and gram negative bacteria (e.g., *Salmonella, Escherichia coli, Vibrio* spp.) were not detected, even at $10^9$ cfu/ml, are provided by FIG. 4B.

The primer set (one or more primer pair) provided herein for detection of all *Listeria* species other than *L. grayi* can be termed a "semi-universal" primer set since the set provides for detection of multiple *Listeria* species. Similarly, primer/probe sets provided herein for detection of all *Listeria* species other than *L. grayi* can be termed a "semi-universal" primer/probe set since the set provides for detection of multiple *Listeria* species. A duplexed TAQMAN® probe-based assay for detection of all species of *Listeria* including *L. grayi*, provides one signal when the probes are labeled with the same fluorescent dye, and provides two signals when the probe for detection of *Listeria grayi* has a different dye that the probe for other *Listeria* species. Thus, *L. grayi* can be differentiated from other *Listeria* species by a duplexed assay.

A "kit," as used herein, refers to a combination of at least some items for performing a PCR assay for *Listeria* spp detection. Embodiments of kits may comprise at least one or more of the following reagents: at least one set of primers specific for *Listeria* spp detection, at least one probe (e.g. a TAQMAN® probe) specific for *Listeria* spp detection, an internal positive control DNA to monitor presence of PCR inhibitors from various food and environmental sources, a baseline control, reagents for sample collection, reagents for isolating nucleic acid such as particles, columns, magnetic beads, lysis buffers, wash buffers, elution buffers, proteases, a DNA polymerase or an enzymatically active mutant or variant thereof, a DNA polymerase buffer, deoxyribonucleotides dATP, dCTP, dGTP, or dTTP. In certain kit embodiments, amplification primers are attached to a solid support such as a microarray.

The container means of the kits will generally include at least one vial, test tube, flask, bottle, syringe or other packaging means, into which a component can be placed, and in some embodiments, suitably aliquoted. Where more than one component is included in the kit (they can be packaged together), the kit also will generally contain at least one second, third or other additional container into which the additional components can be separately placed. However, various combinations of components can be packaged in a container means. The kits of the present teachings also will typically include reagent containers in close confinement for commercial sale. Such containers can include injection or blow-molded plastic containers into which the desired container means are retained. When the components of the kit are provided in one and/or more liquid solutions, the liquid solution comprises an aqueous solution that can be a sterile aqueous solution.

In certain embodiments, at least one kit component is lyophilized and provided as dried powder(s). For example, primers and TAQMAN® probes may be lyophilized. When reagents and/or components are provided as a dry powder, the powder can be reconstituted by the addition of a suitable solvent. In certain embodiments, the solvent is provided in another container means. Kits can also comprise an additional container means for containing a sterile, pharmaceutically acceptable buffer and/or other diluent.

A kit can also include instructions for employing the kit components as well as the use of any other reagent not included in the kit. Instructions can include variations that can be implemented.

An exemplary kit may comprise one or more compositions for detecting one or more *Listeria* species or strains and may comprise at least one primer pair having hybridization specificity for amplifying a rnpB gene of the one or more *Listeria* species, or for amplifying a fragment of the rnpB gene of *Listeria* species.

In one embodiment, a kit may be a kit for detection of *Listeria grayi*. An example kit for detecting *Listeria grayi* may comprise a primer pair of isolated nucleic acid molecules having SEQ ID NO:5 and SEQ ID NO:6; or SEQ ID NO:31 and SEQ ID NO:32; or SEQ ID NO:34 and SEQ ID NO:35; or SEQ ID NO: 37 and SEQ ID NO:38; or SEQ ID NO:40 and SEQ ID NO:41; or SEQ ID NO:43 and SEQ ID NO:44; or SEQ ID NO:46 and SEQ ID NO:47; or a nucleic acid molecule with at least 90% sequence homology to said SEQ ID NOs described; or a labeled derivatives thereof; or various combinations of said primer pairs that are operable to amplify a rnpB gene of *Listeria grayi*, or to amplify a fragment of the rnpB gene of *Listeria grayi*.

In one embodiment, a kit may be a kit for detection of a variety of *Listeria* spp. (including for example, *L. monocytogenes, L. innocua, L. ivanovii, L. welshimerii, L. marthii* and *L. seeligeri*). An example kit for detecting *Listeria* spp may comprise a primer pair of isolated nucleic acid molecules having a primer pair having hybridization specificity for amplifying a conserved rnpB gene of *Listeria* species or a fragment thereof, such as SEQ ID NO:1 or a fragment thereof. An exemplary kit for amplifying SEQ ID NO: 1 or a fragment thereof may comprise a primer pair comprising isolated nucleic acid sequences having SEQ ID NO:2 and SEQ ID NO:3, or a nucleic acid molecule with at least 90% sequence homology to said SEQ ID sequences, or a labeled derivative thereof. This kit embodiment may further comprise an isolated nucleic acid molecule consisting of SEQ ID NO:4, or a nucleic acid molecule with at least 90% sequence homology to said SEQ ID sequence, or a labeled derivative thereof, which may be further used as a probe for detecting amplified SEQ ID NO: 1 or a fragment thereof.

In other kit embodiments, the primer pair having hybridization specificity for amplifying a rnpB gene of *Listeria* species, or for amplifying a fragment of the rnpB gene of *Listeria* species, comprises isolated nucleic acid sequences consisting of SEQ ID NO:8 and SEQ ID NO:9, or SEQ ID NO:11 and SEQ ID NO:12, or SEQ ID NO:14 and SEQ ID NO:15, or SEQ ID NO:17 and SEQ ID NO:18, or SEQ ID NO:20 and SEQ ID NO:21, or SEQ ID NO:22 and SEQ ID NO:23, or SEQ ID NO:25 and SEQ ID NO:26, or SEQ ID NO:28 and SEQ ID NO:29, or a nucleic acid molecule with at least 90% sequence homology to said SEQ ID sequences.

The kit may comprise isolated nucleic acid molecules consisting of SEQ ID NO:5 and SEQ ID NO:6, and the kit may further comprise an isolated nucleic acid molecule consisting of SEQ ID NO:7, or a nucleic acid molecule with at least 90% sequence homology to said SEQ ID sequences. In one embodiment, the primer pair has hybridization specificity for amplifying SEQ ID NO:1, or a fragment thereof, and comprises isolated nucleic acid sequences consisting of SEQ ID NO:2 and SEQ ID NO:3, and wherein the kit further comprises isolated nucleic acid molecules consisting of SEQ ID NO:5, SEQ ID NO:6, and SEQ ID NO:7, or a nucleic acid molecule with at least 90% sequence homology to said SEQ ID sequences.

In an embodiment, a kit comprises isolated nucleic acid molecules consisting of SEQ ID NO:2, SEQ ID NO:3, and SEQ ID NO:4, or a nucleic acid molecule with at least 90% sequence homology to said SEQ ID sequences. In a further embodiment, a kit comprises isolated nucleic acid molecules consisting of SEQ ID NO:5, SEQ ID NO:6, and SEQ ID NO:7, or a nucleic acid molecule with at least 90% sequence homology to said SEQ ID sequences.

In some embodiments a kit of the disclosure may comprise primer pairs (and optionally corresponding probes) for a duplexed assay as described in embodiments above. For example a kit for a duplexed assay to determine all *Listeria* species including *L. grayi* may have primers and probes described in SEQ ID NO's:2-7.

In some embodiments, a kit of the disclosure may be created by lyophilizing reagents for a real-time PCR assay (such as primer sequences and optionally probe sequences) together with reagents of a PCR master mix. Kits having these features provide a convenient format since use of such a kit merely requires the addition of sample to the lyophilized kit reagent. Accordingly, in some embodiments, each assay (combination of primer pairs and optionally probes—described as Assay Id No. in Table 1, FIG. 1) may be developed into a kit of the disclosure.

Several kits of the disclosure were tested against a larger inclusion-exclusion panel of bacteria and these methods and data obtained, are described in detail in Example 5 and Tables 7 and 8 in sections below.

Kits of the disclosure were compared to a reference method used to test for *Listeria* spp. in a study called "methods comparison" wherein a food or environmental matrix is spiked with bacteria to determine if a kit is able to detect the bacteria as well as the reference method does and also to analyze kit performance in comparison to the reference method. These method comparison experiments are detailed in Example 6 wherein results obtained from samples analyzed by kits of the present disclosure referred to as the "MicroSEQ® *Listeria* spp. method" were compared to those analyzed by a reference method referred to as "the ISO 11290-1 reference method" using the Mantel-Haenzel chi-square analysis for unmatched test portions. Results of the methods comparison are detailed in FIGS. 5A-5D, Table 11.

Aspects of the present teachings can be further understood in light of the following examples, which should not be construed as limiting the scope of the present teachings in any way.

Example 1

Primer/Probe Sets for Detection of *Listeria* spp other than *L. grayi*

Using bioinformatic comparisons, a portion of the sequence of the rnpB gene was found in common among various *Listeria* species, strains, cultivars, or serovars obtained from the following publicly available data repositories:
>gi|116245144_c3865-3748 *Listeria monocytogenes* FSL J2-064 NZ_AAR001000223;
>gi|113195789_c90201-90084 *Listeria monocytogenes* J0161 cont1.1;
>gi|154756709_c110353-110236 *Listeria monocytogenes* FSL J2-071; NZ_AARN02000030;
>gi|16799079_c2016439-2016322 *Listeria innocua* Clip11262;
>gi|47096469_c1156-1039 *Listeria monocytogenes* str. 1/2a F6854 cont341;
>gi|116246567_c25083-24966 *Listeria monocytogenes* F6900 cont2.23;
>gi|83316099_c1943002-1942885 *Listeria monocytogenes* str. 4b F2365;
>gi|116740300_c1937597-1937480 *Listeria welshimeri* serovar 6b str. SLCC5334;
>gi|116235920_c8524-8407 *Listeria monocytogenes* FSL J1-175 NZ_AARK01000249;
>gi|116871422_c1937597-1937480 *Listeria welshimeri* serovar 6b str. SLCC5334;
>gi|16246607_c90534-90417 *Listeria monocytogenes* J2818 cont1.27;
>gi|16414292_c226439-226322 *Listeria innocua* Clip11262, segment 8/12;
>gi|116177039_c90674-90557 *Listeria monocytogenes* FSL R2-503 NZ_AARR01000032;
>gi|117671632_c92115-91998 *Listeria monocytogenes* HPB2262 cont2.27;
>gi|119675244_c90575-90458 *Listeria monocytogenes* FSL N1-017 contg2.48;
>gi|47094186_317-434 *Listeria monocytogenes* str. 4b H7858 cont611;
>emb|AL592022.1|_c2016439-2016322 *Listeria innocua* Clip11262;
>gi|16246535_c91967-91850 *Listeria monocytogenes* FSL N3-165 cont2.27;
>emb|AL591824.1|_c1962021-1961904 *Listeria monocytogenes* strain EGD;
>gi|85700163_c1943002-1942885 *Listeria monocytogenes* str. 4b F2365;
>gi|16411141_c209021-208904 *Listeria monocytogenes* strain EGD, complete genome, segment 9/12;
>gi|116176914_c107668-107551 *Listeria monocytogenes* FSL J1-194 NZ_AARJ01000030;
>gi|116243948_c372-255 *Listeria monocytogenes* FSL J1-208 NZ_AARL01000942;
>gi|16802048_c1962021-1961904 *Listeria monocytogenes* EGD-e;
>gi|116247204_c408-291 *Listeria monocytogenes* L028 NZ_AARY01000376;
>gi|113195843_c90456-90339 *Listeria monocytogenes* 10403S cont1.3; and
>gi|116244805_c2408-2291 *Listeria monocytogenes* FSL J2-003 NZ_AARM01000296.

Various PCR amplification primers and TAQMAN® assays were designed against the rnpB sequences and designated assay number 24728, 24729, 23800, 23801, 24107, 24108, and 24109 (See FIG. 1, which describes a column with Assay ID numbers).

Sequences were also obtained in-house for the rnpB gene of five *L. ivanovii* strains:
ATCCBAA-139 *Listeria ivanovii* subsp. *ivanovii*,
ATCC49953 *Listeria ivanovii* subsp. *londoniensis*,
ATCC700402 *Listeria ivanovii* subsp. *ivanovii*,
ATCC19119 *Listeria ivanovii* subsp. *ivanovii*, and
ATCC49954 *Listeria ivanovii* subsp. *londoniensis*.

The *Listeria ivanovii* sequences were found to have ~96% identity with the publicly available *L. monocytogenes* rnpB sequences. Taking the publicly available data together with the *Listeria ivanovii* data, a 118 nucleotide segment of the rnpB gene designated SEQ ID NO:1 (See FIG. 1) was found to be perfectly conserved among the rnpB sequences.

PCR amplification primers and a TAQMAN® probe assays were designed against SEQ ID NO:1 and designated as assay id no. 24728 (See FIG. 1). In one embodiment for identifying SEQ ID NO:1, a forward primer has the sequence 5'-CGAAGTTCCGGCAGAAATGC-3' (SEQ ID NO:2), a reverse primer has the sequence 5'-TGCCCCTAC-CATAAGTTTGAGTTTC-3' (SEQ ID NO:3), and a Taq-Man® probe has the sequence 5'-ACCTCGTTCCACT-TCCG-3' (SEQ ID NO:4). The amplicon size is 118 nucleotides, the predicted melting temperatures of the forward, reverse and MGB probe are 62.14° C., 69.93° C., and 62.16° C., respectively.

DNA sequence alignment analyses have confirmed that each of these primers and probe has a perfect match in each of the above mentioned *Listeria* sequences. Alignment of this combination of oligonucleotides against the microbial subset of the GenBank database did not reveal any significant matches to organisms other than *Listeria* spp.

Table 2 provides a summary of the TaqMan® assay data using the above-cited primer/probe set on several *Listeria* species isolates.

TABLE 2

| Sample Name | $C_T$ |
|---|---|
| PE63 L. monocytogenes | 27.6824 |
| PE64 L. monocytogenes | 28.7945 |
| PE65 L. monocytogenes | 27.3511 |
| PE66 L. monocytogenes | 28.4968 |
| PE67 L. monocytogenes | 26.725 |
| PE68 L. monocytogenes | 27.0546 |
| PE69 L. monocytogenes | 28.1348 |
| PE77 L. monocytogenes | 26.047 |
| PE78 L. monocytogenes | 35.3295 |
| PE79 L. monocytogenes | 27.4459 |
| PE80 L. monocytogenes | 26.8338 |
| PE81 L. monocytogenes | 27.4429 |
| PE82 L. monocytogenes | 28.1586 |
| PE83 L. monocytogenes | 25.1146 |
| PE84 L. monocytogenes | 26.1991 |
| PE85 L. monocytogenes | 26.4452 |
| PE86 L. monocytogenes | 26.2936 |
| PE87 L. monocytogenes | 27.8738 |
| PE88 L. monocytogenes | 25.7468 |
| PE89 L. monocytogenes | 26.3871 |
| PE90 L. monocytogenes | 25.187 |
| PE91 L. monocytogenes | 26.3776 |
| Water | ND |
| Water | ND |
| PE148 L. innocua | 29.6011 |
| PE149 L. innocua | 27.3404 |
| PE150 L. innocua | 26.2744 |
| PE151 L. innocua | 23.8541 |
| PE152 L. innocua | 25.3545 |
| PE 169 L. innocua | 26.8873 |
| PE 170 L. innocua | 23.3046 |
| PE285 L. innocua | 25.0126 |
| PE289 L. innocua | 28.332 |
| PE290 L. innocua | 26.6624 |
| PE291 L. innocua | 20.5618 |
| PE294 L. innocua | 30.0636 |
| PE295 L. innocua | 25.6843 |
| PE296 L. innocua | 22.7243 |
| PE382 L. innocua | 25.9706 |
| PE383 L. innocua | 24.5669 |
| PE384 L. innocua | 25.2329 |
| PE385 L. innocua | 23.3219 |
| PE386 L. innocua | 24.8646 |
| PE387 L. innocua | 25.0642 |
| PE388 L. innocua | 27.0779 |
| PE407 L. innocua | 29.1426 |
| PE411 L. innocua | 20.0159 |
| PE177 L. grayi | ND |
| PE165 L. seeligeri | 22.9871 |
| PE173 L. seeligeri | 21.8677 |
| PE174 L. seeligeri | 25.4094 |
| PE286 L. seeligeri | 21.2432 |
| PE409 L. seeligeri | 24.4277 |
| PE425 L. seeligeri | 22.5709 |
| PE172 L. ivanovii | 24.2454 |
| PE292 L. ivanovii | 23.5624 |
| PE175 L. welshimeri | 24.6152 |
| PE178 L. welshimeri | 25.011 |
| PE424 L. welshimeri | 25.4291 |
| PE426 L. welshimeri | 24.0769 |
| PE1227 L. ivanovii | 23.597 |
| PE1228 L. ivanovii | 23.6289 |
| PE1229 L. ivanovii | 24.2157 |
| PE1230 L. ivanovii | 25.837 |
| PE1231 L. ivanovii | 25.0875 |
| PE1232 L. grayii | ND |
| PE1233 L. grayi | ND |
| PE1234 L. grayi | ND |
| PE1235 L. grayi | ND |
| PE1236 L. grayi | ND |
| PE1237 L. grayi | ND |
| Water | 38.3594 |
| PE1227 L. ivanovii | 23.4601 |
| PE1228 L. ivanovii | 23.1528 |
| PE1229 L. ivanovii | 24.2878 |
| PE1230 L. ivanovii | 25.2483 |
| PE1231 L. ivanovii | 24.2039 |
| PE1232 L. grayi | 39.2089 |

TABLE 2-continued

| Sample Name | $C_T$ |
|---|---|
| PE1233 L. grayi | ND |
| PE1234 L. grayi | ND |
| PE1235 L. grayi | ND |
| PE1236 L. grayi | ND |
| PE1237 L. grayi | ND |
| PE1238 L. innocua | 26.2947 |
| PE1239 L. seeligeri | 26.068 |
| PE1240 L. innocua | 25.5729 |
| PE1241 L. monocytogenes | 24.9592 |
| PE1242 L. monocytogenes | 24.9603 |
| PE1243 L. monocytogenes | 24.6885 |
| PE1244 L. monocytogenes | 25.1274 |
| PE1245 L. welshimeri | ND |
| PE1246 L. welshimeri | 23.9392 |
| PE1247 L. innocua | 24.7399 |
| PE1248 L. monocytogenes | 25.6203 |
| PE1249 L. innocua | 25.1188 |
| PE1250 L. icertae-sedis (now L. marthii) | 23.8687 |

ND—Not Determined, i.e., the amplification signal did not cross the threshold of detection before the end of the run (typically 40 PCR cycles).

The primer/probe set of SEQ ID NO:2-SEQ ID NO:4 are thereby operable for use in assays to identify the following Listeria species: L. monocytogenes, L. innocua, L. welshimeri, L. seelgeri, L. marthii (formerly incertae-sedis) and L. ivanovii.

However, as shown by the data of Table 2, the above primer and probe set is not specific for Listeria grayi.

Example 2

Primer/Probe Sets for Detection of Listeria grayi

The rnpB gene from four Listeria grayi strains (ATCC25402, ATCC25403, ATCC700545, and ATCC25401) obtained from the ATCC were sequenced (ATCC, American Type Culture Collection, Manassas, Va.). Using bioinformatic comparisons, a specific region of the rnpB gene was identified that can be used in specifically detecting the Listeria grayi species. Various PCR amplification primers and TaqMan® assays were designed against specific target areas of the rnpB gene specific to L. grayi and tested for specificity. In one embodiment, a forward primer has the sequence 5'-CCAAACTCTGACGGCAGGTAA-3' (SEQ ID NO:5), a reverse primer has the sequence 5'-ACTTCGTCACTGTGGCACTTT-3' (SEQ ID NO:6), and a probe has the sequence 5'-CAAGGCTACTACATCATATCT-3' (SEQ ID NO:7) (see FIG. 1, Assay 24729).

This primer and probe set has been shown to be highly specific for Listeria grayi and provides highly specific assay results for the rapid detection of the above species from purified genomic DNA.

Experimental research has confirmed that these primers and probe have a perfect match in Listeria grayi, while sequencing data show that the above primer and probe set is not specific for the following Listeria species: Listeria monocytogenes, Listeria ivanovii, Listeria seeligeri, Listeria innocua, incertae-sedis and Listeria welshimeri. The predicted melting temperature of the forward primer, the reverse primer and the MGB probe are 62.07° C., 69.35° C., and 62.21° C., respectively.

Table 3 provides a summary of the TaqMan® assay data produced using the primer/probe set of SEQ ID NO's: 5-7 on genomic DNA isolated from each of the listed Listeria species and strains.

TABLE 3

| Sample Name | $C_T$ |
| --- | --- |
| PE63 L. monocytogenes | ND |
| PE64 L. monocytogenes | ND |
| PE65 L. monocytogenes | ND |
| PE66 L. monocytogenes | ND |
| PE67 L. monocytogenes | ND |
| PE68 L. monocytogenes | ND |
| PE69 L. monocytogenes | ND |
| PE77 L. monocytogenes | ND |
| PE78 L. monocytogenes | ND |
| PE79 L. monocytogenes | ND |
| PE80 L. monocytogenes | ND |
| PE81 L. monocytogenes | ND |
| PE82 L. monocytogenes | ND |
| PE83 L. monocytogenes | ND |
| PE84 L. monocytogenes | ND |
| PE 85 L. monocytogenes | ND |
| PE86 L. monocytogenes | ND |
| PE87 L. monocytogenes | ND |
| PE88 L. monocytogenes | ND |
| PE89 L. monocytogenes | ND |
| PE90 L. monocytogenes | ND |
| PE91 L. monocytogenes | ND |
| water | ND |
| Water | ND |
| PE148 L. innocua | ND |
| PE149 L. innocua | ND |
| PE150 L. innocua | ND |
| PE151 L. innocua | ND |
| PE152 L. innocua | ND |
| PE169 L. innocua | ND |
| PE170 L. innocua | ND |
| PE285 L. innocua | ND |
| PE289 L. innocua | ND |
| PE 290 L. innocua | ND |
| PE291 L. innocua | ND |
| PE294 L. innocua | ND |
| PE295 L. innocua | ND |
| PE296 L. innocua | ND |
| PE382 L. innocua | ND |
| PE383 L. innocua | ND |
| PE 384 L. innocua | ND |
| PE385 L. innocua | ND |
| PE386 L. innocua | ND |
| PE387 L. innocua | 39.6204 |
| PE388 L. innocua | ND |
| PE407 L. innocua | ND |
| PE411 L. innocua | ND |
| PE177 L. grayi | ND |
| PE165 L. seeligeri | ND |
| PE173 L. seeligeri | ND |
| PE174 L. seeligeri | ND |
| PE286 L. seeligeri | ND |
| PE409 L. seeligeri | ND |
| PE425 L. seeligeri | ND |
| PE172 L. ivanovii | ND |
| PE292 L. ivanovii | ND |
| PE175 L. welshimeri | ND |
| PE178 L. welshimeri | ND |
| PE424 L. welshimeri | ND |
| PE426 L. welshimeri | ND |
| PE1227 L. ivanovii | ND |
| PE1228 L. ivanovii | ND |
| PE1229 L. ivanovii | ND |
| PE1230 L. ivanovii | ND |
| PE1231 L. ivanovii | ND |
| PE1232 L. grayi | 27.3642 |
| PE1233 L. grayi | 29.4806 |
| PE1234 L. grayi | 29.9393 |
| PE1235 L. grayi | 29.0728 |
| PE1236 L. grayi | 27.0099 |
| PE1237 L. grayi | 29.2237 |
| Water | ND |
| PE1227 L. ivanovii | ND |
| PE1228 L. ivanovii | ND |
| PE1229 L. ivanovii | ND |
| PE1230 L. ivanovi | ND |
| PE1231 L. ivanovii | ND |
| PE1232 L. grayi | 26.6309 |
| PE1233 L. grayi | 28.7347 |
| PE1234 L. grayi | 29.1725 |
| PE1235 L. grayi | 29.373 |
| PE1236 L. grayi | 25.9029 |
| PE1237 L. grayi | 28.2221 |
| Water | ND |
| PE1239 L. seeligeri | ND |
| PE1240 L. innocua | ND |
| PE1241 L. monocytogenes | ND |
| PE1242 L. monocytogenes | ND |
| PE1243 L. monocytogenes | ND |
| PE1244 L. monocytogenes | ND |
| PE1245 L. welshimeri | ND |
| PE1246 L. welshimeri | ND |
| PE1247 L. innocua | ND |
| PE1248 L. monocytogenes | ND |
| PE1249 L. innocua | ND |
| PE1250 L. incertae-sedis (now L. marthii) | ND |

ND—Not Determined, i.e., the amplification signal did not cross the threshold of detection before the end of the run (typically 40 PCR cycles)

Example 3

Listeria spp Duplexed Assays

The primers and probes of SEQ ID NO's:2-7 were combined to provide a duplexed form of the assays of Example 1 and Example 2 for detection of Listeria species, i.e.: L. monocytogenes, L. innocua, L. welshimeri, L. seeligeri, L. marthii (formerly incertae-sedis), L. ivanovii, and L. grayi.

Table 4 provides a summary of the TaqMan® assay data using the duplexed assay with primer/probe sets as set forth by SEQ ID NO's 2-7 on extracted gDNA (genomic DNA) from each of the listed Listeria species.

TABLE 4

| Sample Name | $C_T$ |
| --- | --- |
| PE63 L. monocytogenes | 26.5345 |
| PE64 L. monocytogenes | 26.7799 |
| PE65 L. monocytogenes | 26.377 |
| PE66 L. monocytogenes | 27.6483 |
| PE67 L. monocytogenes | 25.6262 |
| PE68 L. monocytogenes | 26.1212 |
| PE69 L. monocytogenes | 27.1485 |
| PE77 L. monocytogenes | 25.1728 |
| PE78 L. monocytogenes | 34.4488 |
| PE79 L. monocytogenes | 26.6156 |
| PE80 L. monocytogenes | 25.7919 |
| PE81 L. monocytogenes | 26.7591 |
| PE82 L. monocytogenes | 28.2007 |
| PE83 L. monocytogenes | 24.9056 |
| PE84 L. monocytogenes | 26.2916 |
| PE85 L. monocytogenes | 26.1163 |
| PE86 L. monocytogenes | 26.1961 |
| PE87 L. monocytogenes | 27.4523 |
| PE88 L. monocytogenes | 25.5866 |
| PE89 L. monocytogenes | 26.2464 |
| PE90 L. monocytogenes | 25.1803 |
| PE91 L. monocytogenes | 26.4893 |
| Water | ND |
| Water | ND |
| PE148 L. innocua | 29.2744 |
| PE149 L. innocua | 27.0243 |
| PE150 L. innocua | 26.1935 |
| PE151 L. innocua | 23.621 |
| PE152 L. innocua | 25.5754 |
| PE 169 L. innocua | 26.278 |
| PE 170 L. innocua | 23.0679 |

TABLE 4-continued

| Sample Name | $C_T$ |
|---|---|
| PE285 L. innocua | 24.7561 |
| PE289 L. innocua | 28.6547 |
| PE290 L. innocua | 26.4725 |
| PE291 L. innocua | 20.1239 |
| PE294 L. innocua | 30.0668 |
| PE295 L. innocua | 25.3441 |
| PE296 L. innocua | 22.4874 |
| PE382 L. innocua | 25.4232 |
| PE383 L. innocua | 24.2006 |
| PE384 L. innocua | 24.6692 |
| PE385 L. innocua | 24.0956 |
| PE386 L. innocua | 24.7376 |
| PE387 L. innocua | 25.0149 |
| PE388 L. innocua | 26.9724 |
| PE407 L. innocua | 29.1585 |
| PE411 L. innocua | 19.7418 |
| PE177 L. grayi | 25.0968 |
| PE165 L. seeligeri | 22.6841 |
| PE173 L. seeligeri | 20.9469 |
| PE174 L. seeligeri | 25.2282 |
| PE286 L. seeligeri | 21.157 |
| PE409 L. seeligeri | 23.8425 |
| PE425 L. seeligeri | 21.8198 |
| PE172 L. ivanovii | 23.8942 |
| PE292 L. ivanovii | 23.2731 |
| PE175 L. welshimeri | 25.2465 |
| PE178 L. welshimeri | 24.7079 |
| PE424 L. welshimeri | 25.3494 |
| PE426 L. welshimeri | 23.7373 |
| PE1227 L. ivanovii | 23.3719 |
| PE1228 L. ivanovii | 23.9587 |
| PE1229 L. ivanovii | 24.8442 |
| PE1230 L. ivanovii | 25.1902 |
| PE1231 L. ivanovii | 24.8222 |
| PE1232 L. grayii | 27.8505 |
| PE1233 L. grayi | 30.0191 |
| PE1234 L. grayi | 30.6037 |
| PE1235 L. grayi | 29.0106 |
| PE1236 L. grayi | 26.8987 |
| PE1237 L. grayi | 29.0227 |
| Water | ND |
| PE1227 L. ivanovii | 23.5459 |
| PE1228 L. ivanovii | 23.2868 |
| PE1229 L. ivanovii | 24.2787 |
| PE1230 L. ivanovii | 25.0826 |
| PE1231 L. ivanovii | 24.0516 |
| PE1232 L. grayi | 27.0309 |
| PE1233 L. grayi | 28.6993 |
| PE1234 L. grayi | 29.409 |
| PE1235 L. grayi | 29.1004 |
| PE1236 L. grayi | 25.8966 |
| PE1237 L. grayi | 28.7522 |
| PE1238 L. innocua | 26.1403 |
| PE1239 L. seeligeri | 27.0265 |
| PE1240 L. innocua | 26.1692 |
| PE1241 L. monocytogenes | 25.0361 |
| PE1242 L. monocytogenes | 24.7952 |
| PE1243 L. monocytogenes | 24.7001 |
| PE1244 L. monocytogenes | 25.003 |
| PE1245 L. welshimeri | ND |
| PE1246 L. welshimeri | 24.4296 |
| PE1247 L. innocua | 24.8105 |
| PE1248 L. monocytogenes | 25.7396 |
| PE1249 L. innocua | 25.4116 |
| PE1250 L. icertae-sedis (now L. marthii) | 24.2977 |

ND—Not Determined, i.e., the amplification signal did not cross the threshold of detection before the end of the run (typically 40 PCR cycles)
* gDNA was obtained from the Pasteur Institute FIG. 4A provides data demonstrating that the Listeria spp. duplexed assay showed 100% specificity to the inclusivity targets analyzed. FIG. 4B provides further data demonstrating that the Listeria spp. duplexed assay did not detect cited gram positive or gram negative bacteria, even at $10^9$ cfu/ml. This duplexed TaqMan® assay detects L. monocytogenes, L. innocua, L. ivanovii, L. welshimerii, L. marthii and L. seeligeri, and L. grayi in a single reaction.

Example 4

Rapid Detection of Listeria Species in Food and Environmental Samples

The duplexed TAQMAN® assay of Example 3 was evaluated for detection of Listeria species from food and environmental samples. The duplexed TAQMAN® assay of Example 3 is also referred to herein as "MicroSEQ® Listeria spp assay."

Food System Performance

Food samples (25 g or 25 ml for liquid samples) including smoked salmon, roast beef, hot dogs, infant formula and milk were spiked with 0.2-2 cfu or 2-10 cfu of bacteria. Samples were homogenized with 225 ml buffered Listeria enrichment broth (Buffered Listeria Enrichment Broth, EMD Chemicals, Gibbstown, N.J.) and incubated at 37° C. for 4 hours, at which time Listeria-selective supplements were added (Listeria Enrichment Supplements, EMD Chemicals, Gibbstown, N.J.). Incubation then continued for a total of 24 hours. The samples were then carried through the automated PrepSEQ™ nucleic acid extraction (Applied Biosystems), and the manual PrepSEQ™ RapidSpin method (Applied Biosystems) and detected using the duplexed TaqMan® Assay provided herein. The samples were also cultured using an ISO standard method for comparison of results.

Table 5 presents data from triplicate tests.

TABLE 5

MicroSEQ® Listeria spp. vs. ISO 11290-1

| | MicroSEQ® Listeria spp. | | | $\chi^{2*}$ (MicroSEQ vs. ISO) PrepSEQ NA | $\chi^{2*}$ (MicroSEQ vs. ISO) Rapidspin |
|---|---|---|---|---|---|
| Inoculation Level* | Automated PrepSEQ NA Confirmed+ | RapidSpin Confirmed+ | ISO Confirmed+ | | |
| DRY INFANT FORMULA | | | | | |
| Low | 17/20 | 17/20 | 14/20 | 1.26 | 1.26 |
| High | 20/20 | 20/20 | 19/20 | 1 | 1 |
| MILK | | | | | |
| Low | 4/20 | 4/20 | 4/20 | 0.14 | 0.14 |
| High | 16/20 | 16/20 | 14/20 | 0.52 | 0.52 |

TABLE 5-continued

| | MicroSEQ® Listeria spp. vs. ISO 11290-1 | | | | |
|---|---|---|---|---|---|
| | MicroSEQ® Listeria spp. | | | $\chi^{2*}$ (MicroSEQ vs. ISO) PrepSEQ NA | $\chi^{2*}$ (MicroSEQ vs. ISO) Rapidspin |
| Inoculation Level* | Automated PrepSEQ NA Confirmed+ | RapidSpin Confirmed+ | ISO Confirmed+ | | |
| | LOX | | | | |
| Low | 13/20 | 13/20 | 12/20 | 0.1 | 0.1 |
| High | 16/20 | 16/20 | 18/20 | 0.76 | 0.76 |
| | HOT DOG | | | | |
| Low | 8/20 | 8/20 | 2/20 | 4.68 | 4.68 |
| High | 19/20 | 19/20 | 11/20 | 8.32 | 8.32 |
| | ROAST BEEF | | | | |
| Low | 0/20 | 1/20 | 0/20 | 0 | 1 |
| High | 8/20 | 8/20 | 9/20 | 0.1 | 0.1 |

*Low - 0.2-2 cfu; High - 2-10 cfu of bacteria

The MicroSEQ® Listeria spp. duplexed assay provided herein demonstrated a level of detection to 0.2-2 cfu of bacteria after 24 hours of enrichment for all food matrices tested.

With Chi-square values of <3.84 for dry infant formula, lox, milk and roast beef, no significant difference was observed between the MicroSEQ® method and the reference method.

For hotdog samples, the MicroSEQ® method was superior to the reference culture method.

Environmental System Performance

Pre-defined areas of environmental surfaces (ceramic, stainless steel, plastic, rubber and sealed concrete) were spiked with 0.2-2 cfu or 2-10 cfu of bacteria in the presence of high background. That is, a high concentration of a nonspecific organism was inoculated along with a low concentration of Listeria, in order to assess specificity of the assay. Surfaces were allowed to dry and sponge or swab wipings were taken. Samples were homogenized with 100 ml (sponge) or 10 ml (swab) of buffered Listeria enrichment broth (Buffered Listeria Enrichment Broth, EMD Chemicals, Gibbstown, N.J.) and incubated at 37 degrees C. for 4 hours, at which time Listeria-selective supplements were added (Listeria Enrichment Supplements, EMD Chemicals, Gibbstown, N.J.). Incubation then continued for a total of 28 hours. The samples were then carried through the automated PrepSEQ™ nucleic acid extraction (Applied Biosystems), the manual PrepSEQ™ RapidSpin method and detected using the duplexed TaqMan® Assay provided herein, and were also cultured using ISO standard methods for comparison of results.

Table 6 presents the data from triplicate tests.

TABLE 6

| | MicroSEQ® Listeria spp. vs. ISO 11290-1 | | | | |
|---|---|---|---|---|---|
| | MicroSEQ® Listeria spp. | | | $\chi^{2*}$ (MicroSEQ vs. ISO) PrepSEQ NA | $\chi^{2*}$ (MicroSEQ vs. ISO) Rapidspin |
| Inoculation Level* | Automated PrepSEQ NA Confirmed+ | RapidSpin Confirmed+ | ISO Confirmed + | | |
| | STAINLESS STEEL | | | | |
| Low | 0/20 | 0/20 | 0/20 | NA | NA |
| High | 7/20 | 7/20 | 9/20 | 0.41 | 0.41 |
| | RUBBER | | | | |
| Low | 10/20 | 10/20 | 7/20 | 0.9 | 0.9 |
| High | 19/20 | 19/20 | 18/20 | 0.35 | 0.35 |
| | CERAMIC | | | | |
| Low | 0/20 | 0/20 | 1/20 | 1 | 1 |
| High | 6/20 | 6/20 | 4/20 | 0.52 | 0.52 |
| | PLASTIC | | | | |
| Low | 2/20 | 2/20 | 0/20 | 2.05 | 2.05 |
| High | 9/20 | 9/20 | 7/20 | 0.41 | 0.41 |
| | CONCRETE | | | | |
| Low | 3/20 | 3/20 | 1/20 | 1.08 | 1.08 |
| High | 9/20 | 9/20 | 8/20 | 0.1 | 0.1 |

*Low - 0.2-2 cfu; High - 2-10 cfu of bacteria

The MicroSEQ® *Listeria* spp. duplexed assay demonstrated detection of fractional positive samples from the stainless steel surface after 28 hours of enrichment. With Chi-square values of <3.84, no significant difference was observed between the MicroSEQ® method and the reference method.

Detection of *Listeria* spp. using the real-time PCR duplexed assay reduced the total time-to-result to less than 28 hours, while allowing for sensitive detection from the complex food and environmental samples. Therefore, the rapid pathogen detection systems provided herein can be used as tools for monitoring food production as well as environmental safety.

Example 5

Inclusivity and Exclusivity Testing

Several methods and kits according to the present disclosure were tested against a larger inclusion-exclusion panel of bacteria. Methods and kits of the present disclosure are also referred to as the "MicroSEQ® *Listeria* spp. method" or "MicroSEQ® *Listeria* spp. assay" or "MicroSEQ® method/assay" or "MicroSEQ® *Listeria* spp. Kit."

A total of 50 different *Listeria* isolates and 31 exclusivity strains were evaluated for test method inclusivity and exclusivity.

Methodology:

A total of 50 different isolates of *Listeria* species were evaluated to establish the inclusivity of the methods and assays described in this disclosure. Isolates were obtained from multiple reference sources (ATCC, Cornell University, NCIMB, NCTC and the University of Vermont). Isolates were enriched in BLEB for 22 to 26 h and analyzed within one log of the limit of detection ($10^4$ CFU/mL) of the assay. The PrepSEQ™ Rapid Spin Sample Preparation Kit was used to prepare the bacterial strains, and samples were analyzed by the MicroSEQ® *Listeria* assay.

A total of 31 exclusivity strains were tested to determine the ability of the methods and assays described here to discriminate target organisms from non-target organisms. The exclusivity panel included a wide variety of gram-positive and gram-negative bacteria. Isolates were enriched in Brain Heart Infusion Broth (BHI) for 22-26 h and analyzed undiluted to achieve a high growth test level. The PrepSEQ™ Rapid Spin Sample Preparation Kit was used to prepare the bacterial strains, and samples were analyzed with the MicroSEQ® *Listeria* assay.

Results:

All 50 inclusivity strains were detected as positive by the MicroSEQ® *Listeria* species assay. For the exclusivity evaluation, 31 out of 31 non-*Listeria* species strains resulted in non-detection. Detailed results for the inclusivity and exclusivity strains are presented in Tables 7 and 8 below.

TABLE 7

Inclusion panel: Results for Detection of *Listeria* speices

| Organism/ Reference Number/ Serotype | Source | MicroSEQ Results | Organism/ Reference Number/ Serotype | Source | MicroSEQ Results | Organism/ Reference Number/ Serotype | Source | MicroSEQ Results |
|---|---|---|---|---|---|---|---|---|
| *Listeria grayi* ATCC# 19120 N/A | Chinchilla Feces | Positive | *Listeria monocytogenes* ATCC# 19115 4B | Human | Positive | *Listeria monocytogenes* ATCC# 49594 1/2A | Not Available | Positive |
| *Listeria grayi* ATCC# 25401 N/A | Standing Corn Stalks and Leaves | Positive | *Listeria monocytogenes* ATCC# 19114 4A | Ruminant Brain | Positive | *Listeria monocytogenes* ATCC# 51782 3A | Cheese, Belgium | Positive |
| *Listeria grayi* ATCC# 25402 N/A | Standing Corn Stalks and Leaves | Positive | *Listeria monocytogenes* ATCC# 51780 1/2B | Cheese, Belgium | Positive | *Listeria monocytogenes* ATCC# BAA-751 1/2B | Not Available | Positive |
| *Listeria grayi* ATCC# 25403 N/A | Standing Corn Stalks and Leaves | Positive | *Listeria monocytogenes* ATCC# 7644 1/2C | Human | Positive | *Listeria monocytogenes* CWD 1552 1/2C | Clinical, England | Positive |
| *Listeria grayi* ATCC# 700545 N/A | Not Available | Positive | *Listeria monocytogenes* CWD 1554 1/2A | Clinical, England | Positive | *Listeria monocytogenes* CWD 1553 1/2C | Clinical, England | Positive |
| *Listeria innocua* NCTC# 10528 4AB | Not Available | Positive | *Listeria monocytogenes* CWD 1586 3B | Clinical, USA | Positive | *Listeria monocytogenes* CWD 1584 1/2B | Clinical, Canada | Positive |
| *Listeria innocua* ATCC# 33090 6A | Cow brain | Positive | *Listeria monocytogenes* CWD 1590 4B | Clinical USA | Positive | *Listeria monocytogenes* CWD 1588 1/2B | Clinical, UK | Positive |
| *Listeria innocua* ATCC# 33091 6B | Human Feces | Positive | *Listeria monocytogenes* CWD 1591 3B | Food, USA | Positive | *Listeria monocytogenes* NCTC# 10890 7 | Human Feces | Positive |
| *Listeria innocua* ATCC# 51742 4B | Cabbage | Positive | *Listeria monocytogenes* CWD 1596 4B | Food, England | Positive | *Listeria seeligeri* ATCC# 35967 1/2B | Soil, Germany | Positive |
| *Listeria innocua* | Cheese, Morocco | Positive | *Listeria monocytogenes* | Food, USA | Positive | *Listeria seeligeri* ATCC# 51334 | Intestinal Content of | Positive |

TABLE 7-continued

Inclusion panel: Results for Detection of *Listeria* speices

| Organism/Reference Number/Serotype | Source | MicroSEQ Results | Organism/Reference Number/Serotype | Source | MicroSEQ Results | Organism/Reference Number/Serotype | Source | MicroSEQ Results |
|---|---|---|---|---|---|---|---|---|
| ATCC# BAA-680 6A | | | CWD 1600 3B | NA | Positive | | Bank Vole | |
| *Listeria innocua* NCTC# 11288 6A | Brain of Cow | Positive | *Listeria monocytogenes* FSL J1-049 3C | Not Available | Positive | *Listeria seeligeri* ATCC# 51335 4A | Not Available | Positive |
| *Listeria ivanovii* ATCC# 19119 5 | Sheep, Bulgaria | Positive | *Listeria monocytogenes* FSL J1-129 4AB | Not Available | Positive | *Listeria seeligeri* NCTC# 11289 6B | Not Available | Positive |
| *Listeria ivanovii* ATCC# 49953 5 | Goat, Belgium | Positive | *Listeria monocytogenes* NCIMB# 13726 4B | Not Available | Positive | *Listeria welshimeri* ATCC# 43551 6A | Human Feces | Positive |
| *Listeria ivanovii* ATCC# 49954 5 | Food, France | Positive | *Listeria monocytogenes* ATCC# 15313 1/2A | Rabbit, England | Positive | *Listeria welshimeri* ATCC# 35897 6B | Plant | Positive |
| *Listeria ivanovii* ATCC# BAA-139 5 | Washing Water | Positive | *Listeria monocytogenes* ATCC# 19116 4C | Chicken, England | Positive | *Listeria welshimeri* ATCC# 43549 6B | Not Available | Positive |
| *Listeria ivanovii* ATCC# BAA-678 5 | Sheep Fetus, Spain | Positive | *Listeria monocytogenes* ATCC# 19117 4D | Sheep, USA | Positive | *Listeria welshimeri* ATCC# 43550 1/2B | Cornfield Soil | positive |
| *Listeria monocytogenes* CWD 1555 1/2A | Clinical England | Positive | *Listeria monocytogenes* ATCC# 19118 4E | Chicken, England | Positive | | | |

TABLE 8

Exclusion panel: Results for Detection of *Listeria* species

| Organism Reference Number | Source | MicroSEQ Results | Organism Reference Number | Source | MicroSEQ Results | Organism Reference Number | Source | MicroSEQ Results |
|---|---|---|---|---|---|---|---|---|
| *Bacillus mycoides* ATCC# 6462 | Soil | Negative | *Klebsiella oxytoca* ATCC# 43165 | Clinical Isolate | Negative | *Rhodococcus equi* ATCC# 6939 | Lung Abscess of Foal | Negative |
| *Brochothrix thermosphacta* ATCC# 11509 | Pork Sausage | Negative | *Klebsiella pneumoniae* ATCC# 13883 | Not Available | Negative | *Salmonella enterica* subsp. *enterica* serovar Typhimurium ATCC# 14028 | Chicken Hearts and Livers | Negative |
| *Carnobacterium divergens* ATCC# 35677 | Minced Beef | Negative | *Kurthia zopfii* ATCC# 10538 | Not Available | Negative | *Salmonella enterica* subsp. *enterica* serovar Choleraesuis ATCC# 10708 | Not Available | Negative |
| *Carnobacterium gallinarum* ATCC# 49517 | Ice Slush from around Chicken Carcasses | Negative | *Lactobacillus casei* ATCC# 11578 | Oral Cavity | Negative | *Staphylococcus aureus* ATCC# 29247 | Not Available | Negative |
| *Carnobacterium maltaromaticum* ATCC# 43224 | Vacuum-Packed Beef | Negative | *Lactobacillus fermentum* ATCC# 9338 | Not Available | Negative | *Staphylococcus epidermidis* ATCC# 12228 | Not Available | Negative |
| *Citrobacter freundii* ATCC# 8090 | Not Available | Negative | *Lactobacillus lactis* ATCC# 4797 | Not Available | Negative | *Staphylococcus haemolyticus* ATCC# 29970 | Human Skin | Negative |

TABLE 8-continued

Exclusion panel: Results for Detection of *Listeria* species

| Organism Reference Number | Source | MicroSEQ Results | Organism Reference Number | Source | MicroSEQ Results | Organism Reference Number | Source | MicroSEQ Results |
|---|---|---|---|---|---|---|---|---|
| *Clostridium sporogenes* ATCC #11437 | Plant (cotton) | Negative | *Lactobacillus plantarum* ATCC# 8014 | Not Available | Negative | *Staphylococcus warneri* ATCC# 29885 | Not Available | Negative |
| *Enterobacter aerogenes* ATCC# 13048 | Sputum | Negative | *Microbacterium testaceum* ATCC# 15829 | Paddy | Negative | *Streptococcus pneumoniae* ATCC# 6302 | Not Available | Negative |
| *Enterobacter sakazakii* ATCC# 51329 | Not Available | Negative | *Micrococcus luteus* ATCC# 7468 | Not Available | Negative | *Streptococcus pyogenes* ATCC# 19615 | Pharynx of child | Negative |
| *Enterococcus faecalis* ATCC# 29212 | Urine | Negative | *Proteus mirabilis* ATCC# 7002 | Urine | Negative | | | |
| *Escherichia coli* ATCC# 8739 | Feces | Negative | *Propionibacterium acnes* ATCC# 11827 | Not Available | Negative | | | |

Example 6

Method Comparison Testing

Kits and methods of the disclosure were compared to a reference method used to test for *Listeria* spp. by a "methods comparison" testing comprising testing several food and environmental matrixes spiked with bacteria to determine if a kit and method of the disclosure is able to detect the bacteria as well as a reference ISO method does and to analyze kit performance in comparison to the reference method. Methods and kits of the present disclosure are referred to herein variously as the "MicroSEQ® *Listeria* spp. method" or "MicroSEQ® *Listeria* spp. assay" or "MicroSEQ® method/assay" or "MicroSEQ® *Listeria* spp. Kit" and the reference ISO method is referred to as "the ISO 11290-1 reference method."

All test portions of each food product were aseptically separated into two 25 g samples. For the test method, samples were enriched in 225 mL BLEB. For the reference method, samples were enriched in 225 mL of Demi-Fraser Broth (DF) according to ISO 11290-1. For method comparison, results obtained from the samples analyzed by the MicroSEQ® *Listeria* spp. method were compared to those analyzed by the ISO 11290-1 reference method using the Mantel-Haenzel chi-square analysis for unmatched test portions.

Methodology:

All food products for this assay were purchased one day prior to initiation and prepared for inoculation in sterile stomacher bags. A background screen of each matrix was conducted prior to inoculation and no natural contamination of the target organisms was detected in the test foods.

A total of 45 samples for each of the five food and five non-food items were analyzed for the method comparison portion of the study. Within each sample set there were 5 uninoculated samples, 20 low-level and 20 high-level samples. The target levels of each strain of *Listeria* used for challenging the food matrices were as follows: 0.2-2 colony forming units (CFU)/25 g for the low level inoculation, 2-10 CFU/25 g for the high level inoculation, and 0 CFU/25 g for the uninoculated control samples. The target levels of each strain of *Listeria* species used for challenging the environmental surfaces were as follows: 0.2-2 colony forming units (CFU) per 5 cm$^2$ and 100 cm$^2$ for the low level inoculation, 2-5 CFU per 5 cm$^2$ and 100 cm$^2$ for the high level inoculation, and 0 CFU for the un-inoculated control samples.

Each food matrix was inoculated with a different strain of *Listeria* species (as indicated in Table 9 below) at 0.2-2 CFU/25 g and 2-5 CFU/25 g. For each food and each inoculation level, approximately 1500 g (1000 g for Method Comparison, 350 g for MPN, and 150 extra grams) of sample was inoculated. A 24 h broth culture inoculum was added to a bulk sample of hot dogs and lox. A bulk sample of roast beef and pasteurized whole milk were inoculated with cultures that had been heat stressed at 50° C. for 10 minutes. The dry infant formula was inoculated with a lyophilized culture that had been stabilized in dry infant formula at room temperature (25° C.) for 7-10 days prior to spiking. The lox, roast beef, and hot dogs were placed into sterile stainless steel bins, inoculated with 2 mL of broth culture, and mixed thoroughly by hand for 10 minutes. The milk was placed in a large stomacher bag, inoculated with 2 mL of broth culture, and shaken for approximately 10 minutes by hand to ensure mixing. The dry infant formula was placed in a large stomacher bag, inoculated with 2 g of lyophilized culture, and shaken for approximately 10 minutes by hand to ensure mixing.

Following inoculation, the inoculated hot dog, roast beef, lox, and pasteurized whole milk samples were held at 2-5° C. for 48-72 h prior to analysis to allow time for the organisms to equilibrate within the sample. Additionally, the samples of dry infant formula were held for 2 weeks at room temperature (25° C.) as per AOAC guidelines prior to testing.

The inoculation level was determined using a 3-tube MPN method. On the day of analysis, triplicate 100 g, 10 g, 1 g and 0.1 g samples were prepared at each inoculum level for each food, enriched in the appropriate medium and confirmed according to the ISO 11290-1 reference method procedures.

The environmental surfaces were obtained from various sources and disinfected prior to inoculation. The plastic surface was plastic cutting boards purchased from a grocery store. The sealed concrete surface was cast specifically for the study and sealed with a USDA-approved product called Seal Hard®. The rubber surface was 45 mm thick rubber sheets that were purchased from a hardware store. The ceramic tiles were also purchased from a hardware store. The stainless steel was food-grade quality and purchased directly from a company specializing in cutting boards. Prior to inoculation of the environmental surfaces, all surfaces were disinfected with the DNA remover ELIMINase®. The surfaces were washed with sterile water, wiped with ethanol, neutralized with NaOH, and rinsed with sterile water a final time. The surfaces were then placed under a UV light for 2 h.

Each environmental surface was inoculated with a different strain of Listeria species as indicated in Table 9 below. Additionally, Enterococcus faecalis ATCC#29212 was added to the stainless steel at 10 times the level of the Listeria species to simulate the performance of the target organism in the presence of a competing microflora. A 24 hour broth culture inoculum was used to inoculate the sampling area, and allowed to dry for 16 to 24 h. Sponges or swabs, moistened with D/E Neutralizing broth, were used to sample the entire test area in both vertical and horizontal motions. Samples were held for 2 h at room temperature prior to analysis.

TABLE 9

Test Foods/Surfaces and Inoculating Organisms

| Matrix | Inoculating Organism |
|---|---|
| Hot dogs | L. ivanovii ATCC 19119 |
| Roast beef | L. innocua 4ab NCTC 10528 |
| Lox | L. monocytogenes 4b ATCC 49594 |
| Pasteurized whole milk | L. welshimeri 6b ATCC 35897 |
| Dry infant formula | L. seeligeri 1/2b ATCC 35967 |
| Stainless steel | L. welshimeri 6a ATCC 43551 |
| Plastic cutting board | L. seeligeri 4a ATCC 51335 |
| Ceramic tile | L. grayi ATCC 19120 |
| Rubber sheets | L. innocua 6a NCTC 11228 |

TABLE 9-continued

Test Foods/Surfaces and Inoculating Organisms

| Matrix | Inoculating Organism |
|---|---|
| Concrete sealed with Seal Hard ® | L. monocytogenes 3c FSL J1-049 |

Statistical Analysis:

A Mantel-Haenszel chi-square analysis was used to compare results obtained from the MicroSEQ® Listeria spp. method to those analyzed by the ISO 11290-1 reference method for each of the five food matrices and five environmental surfaces. The Mantel-Haenszel formula for $\chi^2$ analysis was determined using Table 10.

TABLE 10

Mantel-Haenszel Contingency Table

| | | Confirmed positive | Confirmed negative |
|---|---|---|---|
| Alternative method | Presumed positive | A | B |
| | Presumed negative | C | D |
| Reference method | | E | F |

The Mantel-Haenszel formula for $\chi^2$ analysis is:

$$\chi^2 = \frac{(n-1)(AF - (B+C+D)E)^2}{(A+B+C+D)(A+E)(B+C+D+F)(E+F)}$$

where the values for A through F are determined from Table 9, and n=A+B+C+D+E+F. A $\chi^2$ value less than 3.84 is indicative of no significant difference (i.e. accept the null hypothesis that there is no difference; p<0.05).

For an unpaired study design, the following formulas were used to calculate the relative sensitivity, false negative rate, and false positive rate:

Relative sensitivity=A/E
False negative rate=C/(A+C)
False positive rate=B/(B+D)

The results of the method comparison study are also shown in detail in FIGS. 5A-5D, Table 11.

What is claimed is:

1. A composition comprising:
   a) a primer pair comprising SEQ ID NO:5 and SEQ ID NO:6, nucleic acid molecules with at least 90% sequence homology thereto, or a nucleic acid molecule fully complementary thereto, where at least one of the primers is a covalently labeled derivative; and
   b) at least one covalently labeled derivative of a primer or probe having the sequence comprised in any of SEQ ID NO:2-SEQ ID NO:4 and SEQ ID NO:7-SEQ ID NO:48, a nucleic acid molecule with at least 90% sequence homology to SEQ ID NO:2-SEQ ID NO:4 and SEQ ID NO: 7-SEQ ID NO:48, or a nucleic acid molecule fully complementary thereto,
   wherein the covalently labeled derivative comprises a label selected from the group consisting of a fluorescent moiety, a dye, a radioactive isotope, a chemiluminescent label, a bioluminescent label, an enzyme, and combinations thereof.

2. The composition of claim 1, wherein the fluorescent moiety is a fluorescein dye; a rhodamine dye; or a cyanine dye.

3. The composition of claim 1, wherein the fluorescent moiety comprises a fluor and a quencher pair.

4. The composition of claim 3, wherein the fluor is a fluorescein dye and the quencher molecule is a rhodamine dye.

5. The composition of claim 1, further comprising an intercalating label.

6. A kit comprising:
   at least one lyophilized primer pair having hybridization specificity for amplifying a rnpB gene of Listeria species, a fragment thereof, or a full complement of; and
   at least one lyophilized probe sequence having hybridization specificity to an rnpB gene of Listeria species, a fragment thereof or a full complement thereof; and
   one or more reagents for polymerase chain reaction (PCR),
   where the at least one lyophilized primer pair comprises isolated nucleic acid molecules having the sequences of SEQ ID NO:2 and SEQ ID NO:3, or SEQ ID NO:5 and SEQ ID NO:6, or SEQ ID NO:8 and SEQ ID NO:9, or SEQ ID NO:11 and SEQ ID NO:12, or SEQ ID NO:14 and SEQ ID NO:15, or SEQ ID NO:17 and SEQ ID NO:18, or SEQ ID NO:20 and SEQ ID NO:21, or SEQ ID NO:22 and SEQ ID NO:23, or SEQ ID NO:25 and SEQ ID NO:26, or SEQ ID NO:28 and SEQ ID NO:29, SEQ ID NO:5 and SEQ ID NO:6, or SEQ ID NO:31 and SEQ ID NO:32, or SEQ ID NO:34 and SEQ ID NO:35, or SEQ ID NO:37 and SEQ ID NO:38, or SEQ ID NO:40 and SEQ ID NO:41, or SEQ ID NO:43 and SEQ ID NO:44, or SEQ ID NO:46 and SEQ ID NO:47, a full complement thereof, or a nucleic acid molecule with at least 90% sequence homology thereto, where at least one of the primers of the primer pair is a covalently labeled derivative; and where the at least one lyophilized probe comprises isolated nucleic acid molecules having the sequences of SEQ ID NO:4, or SEQ ID NO:7, or SEQ ID NO:10, or SEQ ID NO:13, SEQ ID NO:16, or SEQ ID NO:19, or SEQ ID NO:22, or SEQ ID NO:24, or SEQ ID NO:27, SEQ ID NO:30, SEQ ID NO:7, or SEQ ID NO:33, or SEQ ID NO:36, or SEQ ID NO:39, or SEQ ID NO:42, or SEQ ID NO:45, or SEQ ID NO:48 a full complement thereof, or a nucleic acid molecule with at least 90% sequence homology thereto, where the probe is a covalently labeled derivative.

7. The kit of claim 6, wherein the reagents for PCR are lyophilized.

8. The kit of claim 6, wherein the labeled derivative comprises a label such as a fluorescent moiety, a dye, a radioactive isotope, a chemiluminescent label, a bioluminescent label, an enzyme, and combinations thereof.

9. The kit of claim 8, wherein the fluorescent moiety is a fluorescein dye; a rhodamine dye; or a cyanine dye.

10. The kit of claim 9, wherein the probe comprises a fluorescent moiety comprising a fluor and a quencher pair.

11. The kit of claim 10, wherein the fluor is a fluorescein dye and the quencher molecule is a rhodamine dye.

12. The kit of claim 6, comprising lyophilized primers and probes having the sequence of SEQ ID NO:2, SEQ ID NO:3, and SEQ ID NO:4, full complements thereof, or sequences with at least 90% sequence homology thereto.

13. The kit of claim 6, comprising lyophilized primers and probes having the sequence of SEQ ID NO:5, SEQ ID NO:6, and SEQ ID NO:7, full complements thereof, or sequences with at least 90% sequence homology thereto, or a labeled derivative thereof.

14. The kit of claim 6, further comprising one or more components selected form an internal positive control DNA, a baseline control, reagents for sample collection, reagents for isolating nucleic acid such as particles, columns, magnetic beads, lysis buffers, wash buffers, elution buffers, proteases, a DNA polymerase or an enzymatically active mutant or variant thereof, a DNA polymerase buffer, deoxyribonucleotides dATP, dCTP, dGTP, or dTTP.

15. The kit of claim 6, wherein the primers are attached to a solid support such as a microarray.

16. A method for determining the presence of Listeria organism in a sample comprising:
contacting the sample with a first primer pair operable to amplify SEQ ID NO:1, a fragment thereof, or a complement thereof, under conditions to generate at least a first amplified nucleic acid; and
contacting the sample with a second primer pair selected from SEQ ID NO:5 and SEQ ID NO:6, or SEQ ID NO:31 and SEQ ID NO:32, or SEQ ID NO:34 and SEQ ID NO:35, or SEQ ID NO: 37 and SEQ ID NO:38, or SEQ ID NO:40 and SEQ ID NO:41, or SEQ ID NO:43 and SEQ ID NO:44, or SEQ ID NO:46 and SEQ ID NO:47, or a nucleic acid molecule with at least 90% sequence homology thereto, under conditions to generate a second amplified nucleic acid; and
detecting at least some of the amplified nucleic acids,
wherein detection of either the first amplified nucleic acid sequence or detection of the second amplified nucleic acid sequence or detection of both is indicative of the presence of a Listeria organism in the sample,
wherein detecting the first amplified nucleic acid is indicative of the presence of Listeria species other than Listeria grayi in the sample,
and wherein detecting at least the second amplified nucleic acid is indicative of the presence of Listeria grayi in the sample.

17. The method of claim 16 wherein the wherein the first primer pair is selected from SEQ ID NO:2 and SEQ ID NO:3, or SEQ ID NO:8 and SEQ ID NO:9, or SEQ ID NO:11 and SEQ ID NO:12, or SEQ ID NO:14 and SEQ ID NO:15, or SEQ ID NO:17 and SEQ ID NO:18, or SEQ ID NO:20 and SEQ ID NO:21, or SEQ ID NO:22 and SEQ ID NO:23, or SEQ ID NO:25 and SEQ ID NO:26, or SEQ ID NO:28 and SEQ ID NO:29, or a nucleic acid molecule with at least 90% sequence homology to said primer pair sequences.

18. The method of claim 16, further comprising contacting the sample with a probe comprising isolated nucleic acid molecules having the sequences of SEQ ID NO:4, or SEQ ID NO:10, or SEQ ID NO:13, SEQ ID NO:16, or SEQ ID NO:19, or SEQ ID NO:22, or SEQ ID NO:24, or SEQ ID NO:27, SEQ ID NO:30, SEQ ID NO:7, or SEQ ID NO:33, or SEQ ID NO:36, or SEQ ID NO:39, or SEQ ID NO:42, or SEQ ID NO:45, or SEQ ID NO:48 a full complement thereof, a nucleic acid molecule with at least 90% sequence homology thereto, or a labeled derivative thereof.

19. The method of claim 18, wherein the method comprises amplification comprising polymerase chain reaction (PCR).

20. The method of claim 19, wherein the PCR is an end-point determination, a quantitative PCR, a real-time PCR, a 5'nuclease assay, or a combination thereof.

21. The method of claim 20, wherein the PCR is a real time PCR.

22. The method of claim 20, wherein the PCR is a 5' nuclease assay.

23. The method of claim 16, wherein detecting the first amplified nucleic acid is indicative of the presence of one or more Listeria spp. including L. monocytogenes, L. innocua, L. welshimeri, L. seelgeri, L. marthii (formerly incertaesedis), and L. ivanovii, and wherein detecting the second amplified nucleic acid is indicative of the presence of L. grayi.

24. The method of claim 16, wherein the contacting with the first primer pair and the second primer pair is simultaneous or sequential.

25. The method of claim 16, wherein the sample is a food sample, a solid food sample, a liquid food sample, a smoked salmon sample, a roast beef sample, a hot dog sample, an infant formula sample, a milk sample, an environmental surface sample, a sample from a ceramic surface, a stainless steel surface, a plastic surface, a rubber surface or a sealed concrete surface, an uncooked food sample such as uncooked meats, fish, poultry vegetables, unpasteurized milk, foods made from unpasteurized milk, or dairy products, or cooked or processed foods such as hot dogs, deli meats, cheeses, poultry, ice cream, smoked fish, or seafood, for example; an environmental sample for detection of Listeria species may be soil, stream water, sewage, plants, or swabs from food processing equipment, or any surface that is involved with food processing.

* * * * *

SEQUENCE LISTING

<160> NUMBER OF SEQ ID NOS: 48

<210> SEQ ID NO 1
<211> LENGTH: 118
<212> TYPE: DNA
<213> ORGANISM: Listeria sp.

<400> SEQUENCE: 1
ccttgaaggt gccacagtga cgaagttccg gcagaaatgc tcggaagtgg aacgaggtaa    60
accccacgag cgagaaactc aaacttatgg tagggcact tttcccgagg aatcaaga     118

<210> SEQ ID NO 2
<211> LENGTH: 20
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 2
cgaagttccg gcagaaatgc                                                      20

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tgcccctacc ataagtttga gtttc                                                25

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
acctcgttcc acttccg                                                         17

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ccaaactctg acggcaggta a                                                    21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
acttcgtcac tgtggcactt t                                                    21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
caaggctact acatcatatc t                                                    21

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 8
aaagcagagg aaagtccatg ct                                            22

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gtttgaccag gcacgatcac                                               20

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
tacgggcatc acagcac                                                  17

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cggaagtgga acgaggtaaa cc                                            22

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ctcgtccctt gttcttgatt cct                                           23

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
accataagtt tgagtttctc                                               20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 14
cccacgagcg agaaactcaa                                                   20

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ctcgtccctt gttcttgatt cct                                               23

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16
aagtgcccct accataagt                                                    19

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cgagcgagaa actcaaactt atggt                                             25

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gcctcgtccc ttgttcttga tt                                                22

<210> SEQ ID NO 19
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
cctcgggaaa agtg                                                         14

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 20
gtgatgcccg tagtgatcg                                                    19

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aacgctctgt aagccatgtt c                                                 21

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cggaagtgga acgaggtaaa cc                                                22

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ggaaaagtgc ccctaccata agtt                                              24

<210> SEQ ID NO 24
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
acgagcgaga aactca                                                       16

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gtgccacagt gacgaagttc                                                   20

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
```

```
gcccctacca taagtttgag tttct                                          25
```

<210> SEQ ID NO 27
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27

```
acttccgagc atttct                                                    16
```

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28

```
aaatgctcgg aagtggaacg a                                              21
```

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29

```
aagtgcccct accataagtt tgag                                           24
```

<210> SEQ ID NO 30
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30

```
ccccacgagc gagaaa                                                    16
```

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31

```
cgtagtgatc gtgcttggtg aaa                                            23
```

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
cctgccgtca gagtttggt                                                19

<210> SEQ ID NO 33
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 33
ctgccttggc ttattg                                                   16

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gtgatcgtgc ttggtgaaac aataa                                         25

<210> SEQ ID NO 35
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ggcactttca aggctactac atcat                                         25

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 36
tacctgccgt cagagttt                                                 18

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
acggcaggta aaccatctaa gtc                                           23

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cttcgtcact gtggcacttt c                                             21

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 39
aaggctacta catcatatct tac                                           23

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ggcaggtaaa ccatctaagt cgtaa                                         25

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gcgttccact tctgacattt ctatc                                         25

<210> SEQ ID NO 42
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 42
tcactgtggc actttc                                                   16

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gccacagtga cgaagttctg at                                            22

<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gcccctacca tagtttgagt ttctc                                         25

```
<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 45
tccacttctg acatttct                                                  18

<210> SEQ ID NO 46
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
cccacgagcg agaaactca                                                 19

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
cacctcttcc cttgttcaat ttcct                                          25

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 48
aagtgcccct accatagtt                                                 19
```